US008735649B2

(12) United States Patent
Fuerstenberg et al.

(10) Patent No.: US 8,735,649 B2
(45) Date of Patent: May 27, 2014

(54) WHEAT HAVING REDUCED WAXY PROTEIN DUE TO NON-TRANSGENIC ALTERATIONS OF A WAXY GENE

(75) Inventors: Susan I Fuerstenberg, Hercules, CA (US); Ann J. Slade, Kenmore, WA (US)

(73) Assignee: Arcadia Biosciences, Inc., Davis, CA (US)

(*) Notice: Subject to any disclaimer, the term of this patent is extended or adjusted under 35 U.S.C. 154(b) by 1754 days.

(21) Appl. No.: 11/004,536

(22) Filed: Dec. 3, 2004

(65) Prior Publication Data

US 2005/0150009 A1 Jul. 7, 2005

Related U.S. Application Data

(60) Provisional application No. 60/526,678, filed on Dec. 3, 2003, provisional application No. 60/571,432, filed on May 14, 2004, provisional application No. 60/620,708, filed on Oct. 19, 2004.

(51) Int. Cl.
*A01H 1/06* (2006.01)
*C12N 15/01* (2006.01)
*A01H 5/10* (2006.01)

(52) U.S. Cl.
USPC .......... 800/270; 800/276; 800/267; 800/284; 800/320.3; 800/266; 435/6.11; 435/441; 435/410

(58) Field of Classification Search
USPC ...................................... 800/264, 270, 320.3
See application file for complete search history.

(56) References Cited

U.S. PATENT DOCUMENTS

| 5,994,075 | A | 11/1999 | Goodfellow |
| 6,696,294 | B1 | 2/2004 | Konzak |
| 2003/0106099 | A1 | 6/2003 | Konzak et al. |
| 2003/0150023 | A1 | 8/2003 | Llucinec et al. |
| 2004/0053236 | A1 | 3/2004 | McCallum et al. |

FOREIGN PATENT DOCUMENTS

| JP | 2003259898 | 9/2003 |
| WO | WO-9815621 | 4/1998 |
| WO | WO 99/65292 | 12/1999 |
| WO | WO-0175167 | 10/2001 |
| WO | WO-02096190 | 12/2002 |

OTHER PUBLICATIONS

Score search results for SED ID Nos. 2, 4 and 6.*
Colbert et al. Plant Physiol 126: 480-484, 2001.*
Morris et al. Crop Sci 41: 934-935, 2001.*
Murai et al. Gene 234: 71-79, 1999.*
Fujita et al. Plant Sci 160: 595-602, 2001.*
Yanagisawa, et al. (2001). "An Alanine to Threonine Change in the Wx-D1 Protein Reduces GBSS I Activity in Waxy Mutant Wheat," Euphytica 121:209-214.
Komugi Integrated Wheat Science Database. "Catalogue of Gene Symbols: Wx-A1," National BioResource Project (NBRP), located at <http://www.shigen.nig.ac.jp/wheat/komugi/genes/symbolDetailAction.do?geneId=1290> visited on May 21, 2007. (1 page).
Komugi Integrated Wheat Science Database. "Catalogue of Gene Symbols: Wx-B1," National BioResource Project (NBRP), located at <http://www.shigen.nig.ac.jp/wheat/komugi/genes/symbolDetailAction.do?geneId=1296> visited on May 21, 2007. (1 page).
Komugi Integrated Wheat Science Database. "Catalogue of Gene Symbols: Wx-D1," National BioResource Project(NBRP), located at <http://www.shigen.nig.ac.jp/wheat/komugi/genes/symbolDetailAction.do?geneId=1303> visited on May 21, 2007. (1 page).
Chen, et al., "A Rapid DNA Minipreparation Method Suitable for AFLP and Other PCR Applications", Plant Molecular Biology Reporter, vol. 17, pp. 53-57, 1999.
Colbert et al., "High-Throughput Screening for Induced Point Mutations", Plant Physiology, vol. 126, pp. 480-484, 2001.
Fujita et al., The Isolation and Characterization of a Waxy Mutant of Diploid Wheat (*Triticum monococcum* L.) Plant Science, vol. 160, pp. 595-602, 2001.
Henikoff and Henikoff, "Using Substitution Probabilities to improve Position-Specific Scoring Matrices", Computer Appl. Bioscience, vol. 12 No. 2, pp. 135-143, 1996.
Innis, et al., "PCR Protocols: A Guide to Methods and Applications", Academic Press Inc., pp. 3-21, 1990.
Li et al., "Integrated Platform for Detection of DNA Sequence Variants Using Capillary Array electrophoresis", Electrophoresis, vol. 23(10), pp. 1499-1511, 2002.
McCallum et al., "Targeted Screening for Induced mutations", Nature Biotechnology, vol. 18, pp. 455-457, Apr. 2000.
McCallum et al., "Targeting Induced Local Lesions in Genomes (Tilling) For Plant Functional Genomics", Plant Physiology, vol. 123, pp. 439-442, Jun. 2000.
Murai et al., "Isolation and Characterization Of The Three Waxy Genes Encoding The Granule-Bound Starch Synthase In Hexaploid Wheat", Gene vol. 234, pp. 71-79, 1999.
Nakamura et al., "Production of Waxy (amylose-free) Wheats", Mol. Gen. Genet. vol. 248, pp. 253-259, 1995.
Ng and Henikoff, "SIFT: Predicting Amino Acid Changes That Affect Protein Function", Nucleic Acids Research, vol. 31, pp. 3812-3814, 2003.

(Continued)

*Primary Examiner* — David T Fox
*Assistant Examiner* — Lee A Visone
(74) *Attorney, Agent, or Firm* — Morrison & Foerster LLP

(57) ABSTRACT

A series of independent non-transgenic mutations found at the waxy loci of wheat; wheat plants having these mutations in their waxy loci; and a method of creating and finding similar and/or additional mutations of the waxy by screening pooled and/or individual wheat plants. The wheat plants of the present invention exhibiting altered waxy activity in the wheat without having the inclusion of foreign nucleic acids in their genomes. The invention also includes food and non-food products as well as non-food products that incorporate seeds from the wheat plants having non-transgenic mutations in one or more waxy genes.

7 Claims, No Drawings

(56) References Cited

OTHER PUBLICATIONS

Slade et al., "A Reverse genetic, Nontransgenic Approach to Wheat Crop Improvement by Tilling", Nature Biotechnology, pp. 1-7, Dec. 2004.
Stewart & Via, "A Rapid CTAB DNA Isolation Technique Useful for RAPD Fingerprinting and Other PCR Applications", Bio Techniques vol. 14 No. 5, pp. 748-749, 1993.
Taylor and Greene, "PARSESNP: A Tool for the Analysis of Nucleotide Polymorphisms", Nucleic Acids Research, vol. 31, No. 13, pp. 3808-3811, 2003.
Urbano et al., "Waxy Proteins in Diploid, Tetraploid and Hexaploid Wheats", Plant Breeding, vol. 121, pp. 465-469, 2002.
Yanagisawa et al., "Detection of Single Nucleotide Polymorphism (SNP) Controlling the Waxy Character in Wheat by Using a Derived Cleaved Amplified Polymorphic Sequence (dCAPS) Marker", Theor Appl Genet, vol. 107, pp. 84-88, 2003.
Yasui, "A New Allele on the Wx-D1 Locus Causes an Altered Flour-pasting Profile of the Low-amylose Bread Wheat (*Triticum aestivum* L.) Mutant, K107Afpp4", Breeding Science, vol. 54, pp. 281-286, 2004.
Yasui et al., "Waxy Bread Wheat Mutants, K107Wx1 and K107Wx2, Have a New Null' Allele on Wx-D1 Locus", Breeding Science vol. 48, pp. 405-407, 1998.
Feuillet et al. (2005). "Map-based Isolation of the Leaf Rust Disease Resistance Gene Lr10 from the Hexaploid Wheat (*Triticum aestivum* L.) Genome," *Proceedings of the National Academy of Sciences USA* 100(25):15253-15258.
Henikoff et al. (2004). "Tilling. Traditional Mutagenesis Meets Functional Genomics," *Plant Physiology* 135:1-7.
Ishikawa et al. (2007). "PCR-based Landmark Unique Gene (PLUG) Markers Effectively Assign Homeologous Wheat Genes to A, B and D Genomes," *BMC Genomics* 8:135.
Raval et al. (Jan. 15-19, 2005). "SNP Discovery and Ld Analysis Along A Bin of Deletion in Bread Wheat (*Triticum aestivum*)," *Plant & Animal Genomes XIII Conference*, San Diego, CA, p. 195.

Stadler. (1929). "Chromosome Number and the Mutation Rate in *Avena* and *Triticum*," *Proceedings of the National Academy of Sciences* 15(12):876-881.
Till et al. (2007). "Discovery of Chemically Induced Mutations in Rice by Tilling," *BMC Plant Biology* 7:19.
International Search Report and Written Opinion mailed on Dec. 5, 2007, for PCT Patent Application No. PCT/US04/40779 filed on Dec. 3, 2004. 11 pages.
Yasui et al. (1997). "Waxy Endosperm Mutants of Bread Wheat (*Triticum aestivum* L.) and Their Starch Properties," Breeding Science 47:161-163.
Australian First Report mailed Aug. 27, 2009, for Australia Patent Application No. 2004296834, filed Dec. 3, 2004. 5 pages.
Namy et al., "Identification of stop codon readthrough genes in *Saccharomyces cerevisiae*", Nucleic Acids Research, vol. 31, No. 9, 2003, pp. 2289-2296.
Namy et al., "Impact of the six nucleotides downstream of the stop codon on translation termination", EMBO Reports, vol. 2, No. 9, 2001, pp. 787-793.
Williams et al., "Genome-wide prediction of stop codon readthrough during translation in the yeast *Saccharomyces cerevisiae*" Nucleic Acids Research, vol. 32, No. 22, 2004, pp. 6605-6616.
Office Action received for European Patent Application No. 04813142.9, mailed on Apr. 14, 2010, 7 pages.
International Preliminary Report on Patentability received for PCT Patent Application No. PCT/US2004/040779, issued on Dec. 16, 2008, 5 pages.
Perry et al. (2003). "A Tilling Reverse Genetics Tool and a Web-Accessible Collection of Mutants of the Legume *Lotus japonicus*," Plant Physiology 131:866-871.
Vrinten et al. (1999). "Molecular characterization of waxy mutations in wheat," Molecular and General Genetics 261:463-471.
Supplementary European Search Report mailed Dec. 8, 2009, for European Patent Application No. 04813142.9, filed Dec. 3, 2004, 6 pages.

\* cited by examiner

WHEAT HAVING REDUCED WAXY PROTEIN DUE TO NON-TRANSGENIC ALTERATIONS OF A WAXY GENE

The present application claims benefit to U.S. Provisional Application No. 60/526,678, filed on 3 Dec. 2003; U.S. Provisional Application No. 60/571,432, filed on 14 May 2004; and U.S. Provisional Application No. 60/620,708, filed on 19 Oct. 2004. The entire contents of each of these applications are incorporated by reference herein in their entirety.

FIELD OF THE INVENTION

This invention concerns non-transgenic mutations at one or more waxy locus of wheat and wheat plants having these non-transgenic mutations in their waxy sequences. This invention further concerns wheat plants having starch with lower amylose and higher amylopectin levels compared to starch from wild type wheat as a result of non-transgenic mutations in at least one of their waxy genes. This invention also concerns a method that utilizes non-transgenic means to create wheat plants having mutations in their waxy genes.

BACKGROUND

The ratio of amylose to amylopectin in starch significantly affects the characteristics and quality of its finished food products including their digestibility, water retention, and resistance to staling. Starches that are high in amylose, a linear polymer, tend to gel when cooked whereas those that are high in amylopectin, a branching polymer, tend to form viscous pastes. Because of their unique physical properties including their pasting properties, solubility, gelling capacity, gel strength, swelling power, and vicosity, low amylose/high amylopectin starches are often used in the food industry to improve the texture and mouth-feel of select food products as well as their freeze-thaw stability.

Amylose synthesis in a variety of plants, including wheat, is regulated for the most part by the enzyme granule-bound starch synthase (GBSSI), also known as waxy protein. The importance of this gene in starch synthesis has been well documented in naturally occurring varieties of GBSSI-deficient rice and corn, termed waxy mutants. Following the commercialization of waxy rice and waxy corn starches, there has been extensive interest by wheat breeders and the U.S. Department of Agriculture to develop waxy wheat lines for use in the food industry as well as other commercial applications. Whereas starch from most traditional wheat cultivars is approximately 24% amylose and 76% amylopectin, starch from full waxy wheat lines (i.e., carrying deletions of all three genes) is almost 100% amylopectin. Potential commercial uses of waxy wheat starch include its use as a sauce thickener, emulsifier, and shelf-life extender. When mixed with traditional wheat flour in bread dough, waxy wheat flour improves crumb texture, freshness, and softness and eliminates the need for shortenings, thereby reducing fat content, unhealthy trans-fatty acids, and cost. Blended with other regular flours, waxy wheat flour improves the texture and tenderness of pasta and noodles, including Japanese udon noodles. In addition to the food industry, high amylopectin starches are important to the paper industry for enhancing the strength and printing properties of paper products and to the adhesive industry as a component of glues and adhesives, especially those used on bottles.

Though breeding programs are underway to develop commercial varieties of waxy wheat, the polyploid nature of the wheat genome combined with homoeologous chromosome pairing has made the identification of waxy wheat mutants through traditional breeding methods difficult. The majority of wheat traded in commerce is *Triticum aestivum* or bread wheat. In this hexaploid, waxy is encoded by three homoeologues, Wx-7A, Wx-4A, and Wx-7D with the chromosomal locations 7AS, 4AL, and 7DS (Murai et al., Isolation and characterization of the three Waxy genes encoding the granule-bound starch synthase in hexaploid wheat. Gene 234: 71-79, 1999). In order to breed full waxy varieties using traditional breeding methods, knock-out mutations of all three homoeologues are required. Although several hundred lines of wheat have been identified that carry one or more mutations in the waxy genes Wx-4A and Wx-7A, only four deletion mutations of Wx-7D have been identified to date in over three thousand wheat lines that have been evaluated. One of these is in a Chinese landrace called Bai Huo, whose genetic heterogeneity makes it less suitable for traditional wheat breeding programs than modern elite cultivars. A cross between a double waxy null, Kanto 107, and the Bai Huo landrace was performed to create the first full waxy null line in wheat (Nakamura et al., *Mol Gen Genet* 248: 253-259, 1995). Despite the recent development of waxy breeding lines using this starting material, commercial varieties of waxy wheat are still not available, presumably due to the difficulty of removing undesirable agronomic traits from exotic germplasm. The paucity of Wx-7D deletion mutations has severely limited the development of commercial waxy wheat lines through traditional breeding.

With the availability of the genetic sequences of the *Triticum aestivum* waxy genes, transgenic technology could be used to modify the expression of targeted proteins like waxy rather than rely on traditional breeding programs for the development of waxy wheat cultivars which could take years. However, public acceptance of genetically modified plants, particularly with respect to plants used for food, is low. Therefore, it would be useful to have additional commercial varieties of full or partial waxy wheat that were not the result of genetic engineering. The availability of multiple allelic mutations within each waxy locus would also allow for the breeding of new, diverse waxy phenotypes showing a spectrum of functional characteristics.

SUMMARY OF THE INVENTION

In one aspect, this invention includes a wheat plant having reduced waxy enzyme activity compared to wild type wheat plants created by the steps of obtaining plant material from a parent wheat plant, inducing at least one mutation in at least one copy of a waxy gene of the plant material by treating the plant material with a mutagen to create mutagenized plant material, culturing the mutagenized plant material to produce progeny wheat plants, analyzing progeny wheat plants to detect at least one mutation in at least one copy of a waxy gene, selecting progeny wheat plants that have reduced waxy enzyme activity compared to the parent wheat plant; and repeating the cycle of culturing the progeny wheat plants to produce additional progeny plants having reduced waxy enzyme activity. In another aspect, this invention includes a wheat plant, flowers, seeds, plant parts, and progeny thereof having reduced waxy enzyme activity compared to the wild type wheat plants wherein the reduced waxy enzyme activity is caused by a non-transgenic mutation in a waxy gene of the wheat plant. In another aspect, this invention includes a plant containing a mutated waxy gene, as well as flowers, seeds, pollen, plant parts and progeny of that plant. In another aspect, this invention includes food and food products as well as non-food products that incorporate starch from wheat plants having reduced waxy enzyme activity caused by a non-transgenic mutation in the waxy gene.

BRIEF DESCRIPTION OF THE SEQUENCE LISTING

SEQ ID NO: 1 shows the *Triticum aestivum* gene for starch synthase (waxy), complete cds. (GenBank Accession Number AB019623). This sequence corresponds to the waxy gene Wx-4A.

SEQ ID NO: 2 shows the protein encoded by SEQ ID NO: 1 (GenBank Accession Number BAA77351).

SEQ ID NO: 3 shows the *Triticum aestivum* gene for starch synthase (waxy), complete cds. (GenBank Accession Number AB019622). This sequence corresponds to the waxy gene Wx-7A.

SEQ ID NO: 4 shows the protein encoded by SEQ ID NO: 3 (GenBank Accession Number BAA77350).

SEQ ID NO: 5 shows the *Triticum aestivum* gene for starch synthase (waxy), complete cds. (GenBank Accession Number AB019624). This sequence corresponds to the waxy gene Wx-7D.

SEQ ID NO: 6 shows the protein encoded by SEQ ID NO: 5 (GenBank Accession Number BAA77352).

SEQ ID NO: 7-20 show the DNA sequences for the starch synthase (waxy) specific primers of the present invention.

DETAILED DESCRIPTION OF PREFERRED EMBODIMENTS

The present invention describes a series of independent non-transgenic mutations in a waxy gene; wheat plants having these mutations in a waxy gene thereof; and a method of creating and identifying similar and/or additional mutations in a waxy gene of wheat. Additionally, the present invention describes wheat plants created by this method having low amylose/high amylopectin starch without the inclusion of foreign nucleic acids in the plants' genomes.

In order to create and identify the waxy mutations and the wheat plants of the present invention, a method known as TILLING® was utilized. See McCallum et al., *Nature Biotechnology*, 18: 455-457, 2000; McCallum et al., *Plant Physiology*, 123: 439-442, 2000; Colbert et al., *Plant Physiol.* 126(2): 480-484, 2001 and U.S. Pat. No. 5,994,075 and 20040053236, all of which are incorporated herein by reference. In the basic TILLING® methodology, plant material, such as seeds, are subjected to chemical mutagenesis, which creates a series of mutations within the genomes of the seeds' cells. The mutagenized seeds are grown into adult M1 plants and self-pollinated. DNA samples from the resulting M2 plants are pooled and are then screened for mutations in a gene of interest. Once a mutation is identified in a gene of interest, the seeds of the M2 plant carrying that mutation are grown into adult M3 plants and screened for the phenotypic characteristics associated with the gene of interest.

For the present invention the hexaploid cultivar Express (a hexaploid variety that naturally lacks the 4A locus) and the tetraploid cultivar Kronos were used. However, any cultivar of wheat having at least one waxy gene with substantial homology to SEQ ID NO: 1, SEQ ID NO: 3, or SEQ ID NO: 5 may be used. The homology between the waxy genes and SEQ ID NO: 1, SEQ ID NO: 3, or SEQ ID NO: 5 may be as low as 60% provided that the homology in the conserved regions of the gene is higher. One of skill in the art may prefer a wheat cultivar having commercial popularity or one having specific desired characteristics in which to create the waxy-mutated wheat plants. Alternatively, one of skill in the art may prefer a wheat cultivar having few polymorphisms, such as an in-bred cultivar, in order to facilitate screening for mutations within the waxy locus.

In one embodiment of the present invention, seeds from wheat plants were mutagenized and then grown into M1 plants. The M1 plants were then allowed to self-pollinate and seeds from the M1 plant were grown into M2 plants, which were then screened for mutations in their waxy loci. An advantage of screening the M2 plants is that all somatic mutations correspond to the germline mutations. One of skill in the art would understand that a variety of wheat plant materials, including but not limited to seeds, pollen, plant tissue or plant cells, may be mutagenized in order to create the waxy-mutated wheat plants of the present invention. However, the type of plant material mutagenized may affect when the plant DNA is screened for mutations. For example, when pollen is subjected to mutagenesis prior to pollination of a non-mutagenized plant, the seeds resulting from that pollination are grown into M1 plants. Every cell of the M1 plants will contain mutations created in the pollen, thus these M1 plants may then be screened for waxy mutations instead of waiting until the M2 generation.

Mutagens that create primarily point mutations and short deletions, insertions, transversions, and or transitions (about 1 to about 5 nucleotides), such as chemical mutagens or radiation, may be used to create the mutations of the present invention. Mutagens conforming with the method of the present invention include, but are not limited to, ethyl methanesulfonate (EMS), methylmethane sulfonate (MMS), N-ethyl-N-nitrosurea (ENU), triethylmelamine (TEM), N-methyl-N-nitrosourea (MNU), procarbazine, chlorambucil, cyclophosphamide, diethyl sulfate, acrylamide monomer, melphalan, nitrogen mustard, vincristine, dimethylnitosamine, N-methyl-N'-nitro-Nitrosoguanidine (MNNG), nitrosoguanidine, 2-aminopurine, 7, 12 dimethyl-benz(a)anthracene (DMBA), ethylene oxide, hexamethylphosphoramide, bisulfan, diepoxyalkanes (diepoxyoctane (DEO), diepoxybutane (BEB), and the like), 2-methoxy-6-chloro-9[3-(ethyl-2-chloro-ethyl)aminopropylamino] acridine dihydrochloride (ICR-170), and formaldehyde. Spontaneous mutations in a waxy gene that may not have been directly caused by the mutagen can also be identified using the present invention.

Any method of plant DNA preparation known to those of skill in the art may be used to prepare the wheat plant DNA for waxy mutation screening. For example, see Chen & Ronald, *Plant Molecular Biology Reporter* 17: 53-57 (1999); Stewart & Via, *Bio Techniques*, 1993, 14: 748-749. Additionally, several commercial kits are available, including kits from Qiagen (Valencia, Calif.) and Qbiogene (Carlsbad, Calif.).

Prepared DNA from individual wheat plants was then pooled in order to expedite screening for mutations in a waxy gene of the entire population of plants originating from the mutagenized plant tissue. The size of the pooled group is dependent upon the sensitivity of the screening method used. Preferably, groups of two or more individuals are pooled.

After the DNA samples were pooled, the pools were subjected to waxy sequence-specific amplification techniques, such as Polymerase Chain Reaction (PCR). For a general overview of PCR, see *PCR Protocols: A Guide to Methods and Applications* (Inns, M., Gelfand, D., Sninsky, J., and White, T., eds.), Academic Press, San Diego (1990). Any primers specific to the waxy loci or the sequences immediately adjacent to the waxy loci may be utilized to amplify the waxy sequences within the pooled DNA sample. Preferably, the primer is designed to amplify the regions of the waxy loci where useful mutations are most likely to arise. Most preferably, the primer is designed to detect exonic regions of the waxy genes. Additionally, it is preferable for the primer to avoid known polymorphic sites in order to ease screening for point mutations. To facilitate detection of PCR products on a gel, the PCR primer may be labeled using any conventional labeling method. In the present invention, primers were designed based upon the waxy sequences, GenBank accession numbers AB019623 (SEQ ID NO: 1), AB019622 (SEQ ID NO: 3), and AB019624 (SEQ ID NO: 5). Exemplary primers (SEQ ID NOs: 7-20) that have proven useful in identifying useful mutations within the waxy sequences are shown below in Table 1.

| SEQ ID NO | NAME | ID | SEQUENCE |
|---|---|---|---|
| 7 | 7A WX 2L | PR-1042 | ACCCGCATGGTGTTTGATAATTTCAGTG |
| 8 | 7A WX 2R | PR-1043 | AGAATGCCACCTAGCCATGAAATGGAGT |
| 9 | 7A WX 3L | PR-1045 | CGCTCTGCATATCAATTTTGCGGTTC |
| 10 | 7A WX 3R | PR-1046 | CCTGCAATGCATTCGATCAGTCAGTC |
| 11 | 7A WX 4L | PR-1048 | GTTCTCCTGGTACGATCGACCGACATT |
| 12 | 7A WX 4R | PR-1049 | ATCGGCCCTTCACTCTTAGTTGTTCCAG |
| 13 | 7D WX 2L | PR-1039 | TCGTCGTCTCAACCTTGATAGGCATGGTGAT |
| 14 | 7D WX 2R | PR-1040 | GAACCGCAAAATTGATATGCCTGTTTCA |
| 15 | 7D WX 3L | PR-0973 | TGAAACAGGCATATCAATTTTGCGGTTC |
| 16 | 7D WX 3R | PR-0974 | TCGATCATTCCTTAGGTCTGCTTGATCG |
| 17 | 4A WX 8L | PR-1426 | CCACCCACACACCCACACAAAGAT |
| 18 | 4A WX 8R | PR-1428 | TTTACACAAGGGATCGACGAGCCTAC |
| 19 | 4A WX 6L | PR-1369 | GGTAAGATCAACAACACCCAGCAGCTA |
| 20 | 4A WX 3R | PR-1306 | AACCAGCAATCACCGGAAGAAATCTTTG |

The PCR amplification products may be screened for waxy mutations using any method that identifies nucleotide differences between wild type and mutant sequences. These may include, for example but not limited to, sequencing, denaturing high pressure liquid chromatography (dHPLC), constant denaturant capillary electrophoresis (CDCE), temperature gradient capillary electrophoresis (TGCE) (Li et al., *Electrophoresis*, 23(10): 1499-1511, 2002, or by fragmentation using enzymatic cleavage, such as used in the high throughput method described by Colbert et al., *Plant Physiology*, 126: 480-484, 2001. Preferably the PCR amplification products are incubated with an endonuclease that preferentially cleaves mismatches in heteroduplexes between wild type and mutant sequences. Cleavage products are electrophoresed using an automated sequencing gel apparatus, and gel images are analyzed with the aid of a standard commercial image-processing program.

Each mutation is evaluated in order to predict its impact on protein function (i.e., completely tolerated to loss-of-function) using bioinformatics tools such as SIFT (Sorting Intolerant from Tolerant; Ng and Henikoff, *Nuc Acids Res* 31: 3812-3814, 2003), PSSM (Position-Specific Scoring Matrix; Henikoff and Henikoff, *Comput Appl Biosci* 12: 135-143, 1996) and PARSESNP (Taylor and Greene, *Nuc Acids Res* 31: 3808-3811, 2003). For example, a SIFT score that is less than 0.05 and a large change in PSSM score (roughly 10 or above) indicate a mutation that is likely to have a deleterious effect on protein function.

Mutations that reduce waxy protein function are desirable. Because of the diverse ways in which wheat starch is used, an allelic series of mutations that result in a spectrum of functional characteristics would be useful. Preferred mutations include missense, splice junction, and nonsense changes including mutations that prematurely truncate the translation of the waxy protein from messenger RNA, such as those mutations that create a stop codon within the coding region of the waxy gene. These mutations include insertions, repeat sequences, modified open reading frames (ORFs) and, most preferably, point mutations.

Once an M2 plant having a mutated waxy sequence is identified, the mutations are analyzed to determine its affect on the expression, translation, and/or activity of the waxy enzyme. First, the PCR fragment containing the mutation is sequenced, using standard sequencing techniques, in order to determine the exact location of the mutation in relation to the overall waxy sequence.

If the initial assessment of the mutation in the M2 plant appears to be of a useful nature and in a useful position within the waxy sequence, then further phenotypic analysis of the wheat plant containing that mutation is pursued. First, the M2 plant is backcrossed or outcrossed twice in order to eliminate background mutations. Then the backcrossed or outcrossed plant is self-pollinated in order to create a plant that is homozygous for the waxy mutation. Waxy mutant plants are assessed to determine if the mutation results in a useful phenotypic change including starch type and content, starch characteristics, and seed opaqueness (for example, see Fujita et al., *Plant Science*, 160: 595-602, 2001).

The following mutations in Tables 2 are exemplary of the mutations created and identified according to the present invention. They are offered by way of illustration, not limitation.

Table 2: Examples of Mutations Created and Identified in the Wx-4A, Wx-7A and Wx-7D Waxy Homoeologs of Wheat.

TABLE 2

| Type of Mutation | Variety | WAXY Gene | Primer SEQ IDs. | EMS Treatment | Nucleotide Mutation | Amino Acid Mutation | Nucleotide Numbered According to SEQ ID NO: | Amino Acid Numbered According to SEQ ID NO: |
|---|---|---|---|---|---|---|---|---|
| Truncation | Express | 7A | 7 and 8 | 0.75% | C852T | Q189* | 3 | 4 |
| Truncation | Express | 7D | 13 and 14 | 0.75% | C890T | Q197* | 5 | 6 |
| Truncation | Kronos | 7A | 9 and 10 | 0.075% | G1572A | W354* | 3 | 4 |

TABLE 2-continued

| Type of Mutation | Variety | WAXY Gene | Primer SEQ IDs. | EMS Treatment | Nucleotide Mutation | Amino Acid Mutation | Nucleotide Numbered According to SEQ ID NO: | Amino Acid Numbered According to SEQ ID NO: |
|---|---|---|---|---|---|---|---|---|
| Missense | Kronos | 4A | 19 and 20 | 0.075% | G1115A | V224M | 1 | 2 |
| Missense | Kronos | 4A | 19 and 20 | 0.075% | C1140T | T232M | 1 | 2 |
| Missense | Kronos | 4A | 17 and 18 | 0.075% | G1993A | G434E | 1 | 2 |
| Missense | Kronos | 4A | 17 and 18 | 0.075% | C2040T | P450S | 1 | 2 |
| Missense | Kronos | 4A | 17 and 18 | 0.075% | G2053A | R454K | 1 | 2 |
| Missense | Kronos | 4A | 17 and 18 | 0.075% | C2154T | L488F | 1 | 2 |
| Missense | Kronos | 4A | 17 and 18 | 0.075% | G2161A | G490E | 1 | 2 |
| Missense | Express | 7A | 7 and 8 | 0.75% | G832A | G182D | 3 | 4 |
| Missense | Express | 7A | 7 and 8 | 0.75% | C858T | R191C | 3 | 4 |
| Missense | Express | 7A | 7 and 8 | 0.75% | G882A | A199T | 3 | 4 |
| Missense | Express | 7A | 7 and 8 | 0.75% | C922T | P212L | 3 | 4 |
| Missense | Express | 7A | 7 and 8 | 1.00% | G1070A | E220K | 3 | 4 |
| Missense | Express | 7A | 7 and 8 | 1.00% | G1107A | G232D | 3 | 4 |
| Missense | Express | 7A | 7 and 8 | 0.75% | C1116T | A235V | 3 | 4 |
| Missense | Express | 7A | 7 and 8 | 0.75% | C1143T | S244F | 3 | 4 |
| Missense | Express | 7A | 9 and 10 | 0.75% | G1425A | G305E | 3 | 4 |
| Missense | Express | 7A | 9 and 10 | 1.00% | G1533A | G341E | 3 | 4 |
| Missense | Express | 7A | 9 and 10 | 0.75% | G1542A | G344D | 3 | 4 |
| Missense | Express | 7A | 9 and 10 | 0.75% | G1586A | D359N | 3 | 4 |
| Missense | Express | 7A | 9 and 10 | 0.75% | C1595T | L362F | 3 | 4 |
| Missense | Express | 7A | 9 and 10 | 0.75% | C1599T | T363I | 3 | 4 |
| Missense | Express | 7A | 9 and 10 | 0.75% | G1761A | G387R | 3 | 4 |
| Missense | Express | 7A | 9 and 10 | 1.00% | G1770A | V390M | 3 | 4 |
| Missense | Express | 7A | 9 and 10 | 0.75% | C1851T | P417S | 3 | 4 |
| Missense | Express | 7A | 11 and 12 | 0.75% | G1995A | G433E | 3 | 4 |
| Missense | Express | 7A | 11 and 12 | 1.00% | C2042T | P449S | 3 | 4 |
| Missense | Express | 7A | 11 and 12 | 0.75% | G2060A | V455M | 3 | 4 |
| Missense | Express | 7A | 11 and 12 | 0.75% | C2100T | A468V | 3 | 4 |
| Missense | Express | 7A | 11 and 12 | 0.75% | G2103A | G469D | 3 | 4 |
| Missense | Express | 7A | 11 and 12 | 0.75% | G2274A | C496Y | 3 | 4 |
| Missense | Express | 7A | 11 and 12 | 0.75% | C2283T | A499V | 3 | 4 |
| Missense | Express | 7A | 11 and 12 | 0.75% | G2292A | G502D | 3 | 4 |
| Missense | Express | 7A | 11 and 12 | 1.00% | G2315A | E510K | 3 | 4 |
| Missense | Kronos | 7A | 9 and 10 | 0.075% | G1469A | A320T | 3 | 4 |
| Missense | Kronos | 7A | 9 and 10 | 0.075% | C1485T | S325F | 3 | 4 |
| Missense | Kronos | 7A | 9 and 10 | 0.075% | G1490A | E327K | 3 | 4 |
| Missense | Kronos | 7A | 11 and 12 | 0.075% | C2042T | P449S | 3 | 4 |
| Missense | Kronos | 7A | 11 and 12 | 0.075% | C2129T | R478C | 3 | 4 |
| Missense | Kronos | 7A | 11 and 12 | 0.075% | G2162A | G489R | 3 | 4 |
| Missense | Express | 7D | 13 and 14 | 1.00% | G860T | D187Y | 5 | 6 |

TABLE 2-continued

| Type of Mutation | Variety | WAXY Gene | Primer SEQ IDs. | EMS Treatment | Nucleotide Mutation | Amino Acid Mutation | Nucleotide Numbered According to SEQ ID NO: | Amino Acid Numbered According to SEQ ID NO: |
|---|---|---|---|---|---|---|---|---|
| Missense | Express | 7D | 13 and 14 | 0.75% | G879A | S193N | 5 | 6 |
| Missense | Express | 7D | 13 and 14 | 1.00% | G896A | A199T | 5 | 6 |
| Missense | Express | 7D | 13 and 14 | 1.00% | G1109A | G219E | 5 | 6 |
| Missense | Express | 7D | 13 and 14 | 0.75% | G1130A | C226Y | 5 | 6 |
| Missense | Express | 7D | 13 and 14 | 0.75% | G1147A | G232S | 5 | 6 |
| Missense | Express | 7D | 13 and 14 | 1.00% | G1148A | G232D | 5 | 6 |
| Missense | Express | 7D | 13 and 14 | 0.75% | G1160A | C236Y | 5 | 6 |
| Missense | Express | 7D | 13 and 14 | 0.75% | C1184T | S244F | 5 | 6 |
| Missense | Express | 7D | 15 and 16 | 1.00% | G1351A | V253M | 5 | 6 |
| Missense | Express | 7D | 15 and 16 | 0.75% | C1424T | P277L | 5 | 6 |
| Missense | Express | 7D | 15 and 16 | 0.75% | G1507A | G305R | 5 | 6 |
| Missense | Express | 7D | 15 and 16 | 0.75% | G1528A | V312M | 5 | 6 |
| Missense | Express | 7D | 15 and 16 | 0.75% | C1535T | T314M | 5 | 6 |
| Missense | Express | 7D | 15 and 16 | 0.75% | G1558A | E322K | 5 | 6 |
| Missense | Express | 7D | 15 and 16 | 0.75% | C1622T | T343I | 5 | 6 |
| Missense | Express | 7D | 15 and 16 | 0.75% | G1625A | G344D | 5 | 6 |
| Missense | Express | 7D | 15 and 16 | 0.75% | G1630A | V346I | 5 | 6 |
| Missense | Express | 7D | 15 and 16 | 0.75% | C1661T | P356L | 5 | 6 |
| Missense | Express | 7D | 15 and 16 | 0.75% | C1682T | A363V | 5 | 6 |
| Missense | Express | 7D | 15 and 16 | 0.75% | C1682T | A363V | 5 | 6 |
| Missense | Express | 7D | 15 and 16 | 1.00% | C1844T | P389S | 5 | 6 |
| Missense | Express | 7D | 15 and 16 | 1.00% | C1905T | P409L | 5 | 6 |
| Missense | Express | 7D | 15 and 16 | 0.75% | G1907A | D410N | 5 | 6 |
| Splice Junction | Express | 7A | 11 and 12 | 0.75% | G2180A | Splice | 3 | 4 |
| Splice Junction | Express | 7A | 11 and 12 | 1.00% | G2180A | Splice | 3 | 4 |
| Splice Junction | Express | 7D | 13 and 14 | 1.00% | G957A | Splice | 5 | 6 |
| Splice Junction | Express | 7D | 13 and 14 | 0.75% | G1108A | Splice | 5 | 6 |
| Splice Junction | Express | 7D | 15 and 16 | 0.75% | G1970A | Splice | 5 | 6 |

EXAMPLE 1

Mutagenesis

In one embodiment of the present invention, wheat seeds of the hexaploid cultivar (*Triticum aestivum*) Express and the tetrapolid cultivar (*Triticum turgidum*, Durum) Kronos were vacuum infiltrated in H$_2$O (approximately 1000 seeds/100 ml H$_2$O for approximately 4 minutes). The seeds were then placed on a shaker (45 rpm) in a fume hood at ambient temperature. The mutagen ethyl methanesulfonate (EMS) was added to the imbibing seeds to final concentrations ranging from about 0.75% to about 1.2% (v/v). Following an 18-hour incubation period, the EMS solution was replaced with fresh H$_2$O (4 times). The seeds were then rinsed under running water for about 4-8 hours. Finally, the mutagenized seeds were planted (96/tray) in potting soil and allowed to germinate indoors. Plants that were four to six weeks old were transferred to the field to grow to fully mature M1 plants. The mature M1 plants were allowed to self-pollinate and then seeds from the M1 plant were collected and planted to produce M2 plants.

DNA Preparation

DNA from these M2 plants was extracted and prepared in order to identify which M2 plants carried a mutation at their waxy loci. The M2 plant DNA was prepared using the methods and reagents contained in the Qiagen® (Valencia, Calif.) DNeasy® 96 Plant Kit. Approximately 50 mg of frozen plant sample was placed in a sample tube with a tungsten bead, frozen in liquid nitrogen and ground 2 times for 1 minute each at 20 Hz using the Retsch® Mixer Mill MM 300. Next 400 µl of solution AP1 [Buffer AP 1, solution DX and RNAse (100 mg/ml)] at 80° C. was added to the sample. The tube was sealed and shaken for 15 seconds. Following the addition of 130 µl Buffer AP2, the tube was shaken for 15 seconds. The samples were placed in a freezer at minus 20° C. for at least 1 hour. The samples were then centrifuged for 20 minutes at 5600×g. A 400 µl aliquot of supernatant was transferred to another sample tube. Following the addition of 600 µl of Buffer AP3/E, this sample tube was capped and shaken for 15 seconds. A filter plate was placed on a square well block and 1 ml of the sample solution was applied to each well and the plate was sealed. The plate and block were centrifuged for 4 minutes at 5600×g. Next, 800 µl of Buffer AW was added to each well of the filter plate, sealed and spun for 15 minutes at 5600×g in the square well block. The filter plate was then placed on a new set of sample tubes and 80 µl of Buffer AE was applied to the filter. It was capped and incubated at room temperature for 1 minute and then spun for 2 minutes at 5600×g. This step was repeated with an additional 80 µl Buffer AE. The filter plate was removed and the tubes containing the pooled filtrates were capped. The individual samples were then normalized to a DNA concentration of 5 to 10 ng/µl.

Tilling®

The M2 DNA was pooled into groups of two individual plants. The DNA concentration for each individual within the pool was approximately 0.8 ng/µl with a final concentration of 1.6 ng/µl for the entire pool. Then, 5 µl of the pooled DNA samples 8 ng was arrayed on microtiter plates and subjected to gene-specific PCR.

PCR amplification was performed in 15 µl volumes containing 2.5 ng pooled DNA, 0.75×ExTaq buffer (Panvera®, Madison, Wis.), 2.6 mM $MgCl_2$, 0.3 mM dNTPs, 0.3 µM primers, and 0.05U Ex-Taq (Panvera®) DNA polymerase. PCR amplification was performed using an MJ Research® thermal cycler as follows: heat denaturation at 95° C. for 2 minutes; followed by 8 cycles of "touchdown PCR" (94° C. for 20 second, an annealing step starting at 70-68° C. for 30 seconds and decreasing 1° C. per cycle, a temperature ramp increasing 0.5° C. per second to 72° C., and 72° C. for 1 minute); then 25-45 cycles of PCR (94° C. for 20 seconds, 63-61° C. for 30 seconds, ramp of 0.5° C. per second up to 72° C., 72° C. for 1 minute); and finally extension, denaturation and reannealing steps (72° C. for 8 minutes; 98° C. for 8 minutes; 80° C. for 20 seconds, followed by 60 cycles of 80° C. for 7 seconds decreasing 0.3 degrees/cycle).

The PCR primers (MWG Biotech, Inc., High Point, N.C.) were mixed as follows:
- 2.5 µl 100 µM IRD-700 labeled left primer
- 7.5 µl 100 µM left primer
- 9.0 µl 100 µM IRD-800 labeled right primer
- 1.0 µl 100 µM right primer A label can be attached to each primer as described or to only one of the primers. Alternatively, Cy5.5 modified primers could be used. The IRD-label was coupled to the oligonucleotide using conventional phosphoramidite chemistry.

PCR products (15 µl) were digested in 96-well plates. Next, 30 µl of a solution containing 10 mM HEPES [4-(2-hydroxyethyl)-1-piperazineethanesulfonic acid] (pH 7.5), 10 mM $MgSO_4$, 0.002% (w/v) Triton® X-100, 20 ng/ml of bovine serum albumin, and CEL 1 (Transgenomic®, Inc.; 1:100,000 dilution) was added with mixing on ice, and the plate was incubated at 45° C. for 15 min. The specific activity of the CEL1 was 800 units/µl, where a unit was defined by the manufacturer as the amount of enzyme required to produce 1 ng of acid-soluble material from sheared, heat denatured calf thymus DNA at pH 8.5 in one minute at 37° C. Reactions were stopped by addition of 10 µl of a 2.5 M NaCl solution with 0.5 mg/ml blue dextran and 75 mM EDTA, followed by the addition of 80 µl isopropanol. The reactions were precipitated at 80° C., spun at 4000 rpm for 30 minutes in an Eppendorf Centrifuge 5810. Pellets were resuspended in 8 µl of 33% formamide with 0.017% bromophenol blue dye, heated at 80° C. for 7 minutes and then at 95° C. for 2 minutes. Samples were transferred to a membrane comb using a comb-loading robot (MWG Biotech). The comb was inserted into a slab acrylamide gel (6.5%), electrophoresed for 10 min, and removed. Electrophoresis was continued for 4 h at 1,500-V, 40-W, and 40-mA limits at 50° C.

During electrophoresis, the gel was imaged using a LI-COR® (Lincoln, Nebr.) scanner which was set at a channel capable of detecting the IR Dye 700 and 800 labels. The gel image showed sequence-specific pattern of background bands common to all 96 lanes. Rare events, such as mutations, create new bands that stand out above the background pattern. Plants with bands indicative of mutations of interest were evaluated by TILLING® individual members of a pool mixed with wild type DNA and then sequencing individual PCR products. Plants carrying mutations confirmed by sequencing were grown up as described above (e.g., the M2 plant was backcrossed or outcrossed twice in order to eliminate background mutations and self-pollinated in order to create a plant that was homozygous for the mutation). Mutations identified during TILLING® are shown below in Tables 3 and 4.

TABLE 3

| Gene | Primer SEQ IDs. | EMS Treatment | Nucleotide Mutation According to SEQ ID | Amino Acid Mutation | PSSM Score | SIFT Score | Nucleotide Numbered According to SEQ ID NO: | Amino Acid Numbered According to SEQ ID NO: |
|---|---|---|---|---|---|---|---|---|
| WAXY 7A | 7 and 8 | 0.75% | C791T | V168= | | | 3 | 4 |
| WAXY 7A | 7 and 8 | 0.75% | C792T | R169W | | 1.00 | 3 | 4 |
| WAXY 7A | 7 and 8 | 0.75% | G794A | R169= | | | 3 | 4 |

TABLE 3-continued

| Gene | Primer SEQ IDs. | EMS Treatment | Nucleotide Mutation According to SEQ ID | Amino Acid Mutation | PSSM Score | SIFT Score | Nucleotide Numbered According to SEQ ID NO: | Amino Acid Numbered According to SEQ ID NO: |
|---|---|---|---|---|---|---|---|---|
| WAXY 7A | 7 and 8 | 0.75% | G807A | E174K | | 0.07 | 3 | 4 |
| WAXY 7A | 7 and 8 | 1.00% | G825A | D180N | | 0.50 | 3 | 4 |
| WAXY 7A | 7 and 8 | 0.75% | G832A | G182D | | 0.00 | 3 | 4 |
| WAXY 7A | 7 and 8 | 0.75% | C835T | T183I | | 0.19 | 3 | 4 |
| WAXY 7A | 7 and 8 | 0.75% | C851T | N188= | | | 3 | 4 |
| WAXY 7A | 7 and 8 | 0.75% | C852T | Q189* | | | 3 | 4 |
| WAXY 7A | 7 and 8 | 0.75% | C858T | R191C | 31.1 | 0.00 | 3 | 4 |
| WAXY 7A | 7 and 8 | 0.75% | C860T | R191= | | | 3 | 4 |
| WAXY 7A | 7 and 8 | 1.00% | C860T | R191= | | | 3 | 4 |
| WAXY 7A | 7 and 8 | 0.75% | G882A | A199T | | 0.00 | 3 | 4 |
| WAXY 7A | 7 and 8 | 0.75% | G882A | A199T | | 0.00 | 3 | 4 |
| WAXY 7A | 7 and 8 | 0.75% | C911T | L208= | | | 3 | 4 |
| WAXY 7A | 7 and 8 | 0.75% | C922T | P212L | | 0.00 | 3 | 4 |
| WAXY 7A | 7 and 8 | 0.75% | G947A | Intron | | | 3 | 4 |
| WAXY 7A | 7 and 8 | 0.75% | G994A | Intron | | | 3 | 4 |
| WAXY 7A | 7 and 8 | 0.75% | G996A | Intron | | | 3 | 4 |
| WAXY 7A | 7 and 8 | 0.75% | G1002A | Intron | | | 3 | 4 |
| WAXY 7A | 7 and 8 | 0.75% | G1002A | Intron | | | 3 | 4 |
| WAXY 7A | 7 and 8 | 1.00% | C1011T | Intron | | | 3 | 4 |
| WAXY 7A | 7 and 8 | 0.75% | C1017T | Intron | | | 3 | 4 |
| WAXY 7A | 7 and 8 | 0.75% | C1017T | Intron | | | 3 | 4 |
| WAXY 7A | 7 and 8 | 1.00% | C1018T | Intron | | | 3 | 4 |
| WAXY 7A | 7 and 8 | 0.75% | C1040T | Intron | | | 3 | 4 |
| WAXY 7A | 7 and 8 | 0.75% | C1045T | Intron | | | 3 | 4 |
| WAXY 7A | 7 and 8 | 0.75% | C1050T | Intron | | | 3 | 4 |
| WAXY 7A | 7 and 8 | 0.75% | C1058T | Intron | | | 3 | 4 |
| WAXY 7A | 7 and 8 | 1.00% | C1060T | Intron | | | 3 | 4 |
| WAXY 7A | 7 and 8 | 1.00% | C1060T | Intron | | | 3 | 4 |
| WAXY 7A | 7 and 8 | 0.75% | C1065T | Intron | | | 3 | 4 |
| WAXY 7A | 7 and 8 | 1.00% | G1070A | E220K | 14.8 | 0.00 | 3 | 4 |
| WAXY 7A | 7 and 8 | 1.00% | G1107A | G232D | 12.1 | 0.00 | 3 | 4 |
| WAXY 7A | 7 and 8 | 0.75% | C1112T | L234= | | | 3 | 4 |
| WAXY 7A | 7 and 8 | 0.75% | C1116T | A235V | 17.9 | 0.00 | 3 | 4 |
| WAXY 7A | 7 and 8 | 0.75% | C1143T | S244F | 17.9 | 0.00 | 3 | 4 |
| WAXY 7A | 7 and 8 | 0.75% | G1202A | Intron | | | 3 | 4 |
| WAXY 7A | 7 and 8 | 0.75% | C1216T | Intron | | | 3 | 4 |

TABLE 3-continued

| Gene | Primer SEQ IDs. | EMS Treatment | Nucleotide Mutation According to SEQ ID | Amino Acid Mutation | PSSM Score | SIFT Score | Nucleotide Numbered According to SEQ ID NO: | Amino Acid Numbered According to SEQ ID NO: |
|---|---|---|---|---|---|---|---|---|
| WAXY 7A | 7 and 8 | 1.00% | G1231A | Intron | | | 3 | 4 |
| WAXY 7A | 7 and 8 | 0.75% | G1235A | Intron | | | 3 | 4 |
| WAXY 7A | 7 and 8 | 0.75% | C1279T | C256= | | | 3 | 4 |
| WAXY 7A | 9 and 10 | 0.75% | C1324T | F271= | | | 3 | 4 |
| WAXY 7A | 9 and 10 | 0.75% | G1394A | E295K | −7.9 | 1.00 | 3 | 4 |
| WAXY 7A | 9 and 10 | 1.00% | C1411T | N300= | | | 3 | 4 |
| WAXY 7A | 9 and 10 | 0.75% | G1425A | G305E | 29.6 | 0.00 | 3 | 4 |
| WAXY 7A | 9 and 10 | 1.00% | G1444A | K311= | | | 3 | 4 |
| WAXY 7A | 9 and 10 | 1.00% | C1459T | S316= | | | 3 | 4 |
| WAXY 7A | 9 and 10 | 1.00% | G1533A | G341E | 17.6 | 0.01 | 3 | 4 |
| WAXY 7A | 9 and 10 | 0.75% | G1542A | G344D | 16.0 | 0.00 | 3 | 4 |
| WAXY 7A | 9 and 10 | 1.00% | G1542A | G344D | 16.0 | 0.00 | 3 | 4 |
| WAXY 7A | 9 and 10 | 0.75% | C1561T | D350= | | | 3 | 4 |
| WAXY 7A | 9 and 10 | 0.75% | G1566A | S352N | 8.4 | 0.14 | 3 | 4 |
| WAXY 7A | 9 and 10 | 0.75% | G1585A | K358= | | | 3 | 4 |
| WAXY 7A | 9 and 10 | 0.75% | G1586A | D359N | 28.9 | 0.00 | 3 | 4 |
| WAXY 7A | 9 and 10 | 0.75% | C1595T | L362F | 20.6 | 0.00 | 3 | 4 |
| WAXY 7A | 9 and 10 | 0.75% | C1599T | T363I | 13.7 | 0.15 | 3 | 4 |
| WAXY 7A | 9 and 10 | 0.75% | C1638T | Intron | | | 3 | 4 |
| WAXY 7A | 9 and 10 | 0.75% | C1638T | Intron | | | 3 | 4 |
| WAXY 7A | 9 and 10 | 0.75% | G1647A | Intron | | | 3 | 4 |
| WAXY 7A | 9 and 10 | 0.75% | C1656T | Intron | | | 3 | 4 |
| WAXY 7A | 9 and 10 | 1.00% | G1668A | Intron | | | 3 | 4 |
| WAXY 7A | 9 and 10 | 0.75% | C1693T | Intron | | | 3 | 4 |
| WAXY 7A | 9 and 10 | 0.75% | G1706A | Intron | | | 3 | 4 |
| WAXY 7A | 9 and 10 | 0.75% | G1706A | Intron | | | 3 | 4 |
| WAXY 7A | 9 and 10 | 0.75% | C1736T | N378= | | | 3 | 4 |
| WAXY 7A | 9 and 10 | 0.75% | C1736T | N378= | | | 3 | 4 |
| WAXY 7A | 9 and 10 | 0.75% | G1761A | G387R | 12.0 | 0.01 | 3 | 4 |
| WAXY 7A | 9 and 10 | 1.00% | G1770A | V390M | 15.6 | 0.00 | 3 | 4 |
| WAXY 7A | 9 and 10 | 1.00% | G1778A | R392= | | | 3 | 4 |
| WAXY 7A | 9 and 10 | 0.75% | G1808A | R402= | | | 3 | 4 |
| WAXY 7A | 9 and 10 | 0.75% | C1809T | L403= | | | 3 | 4 |
| WAXY 7A | 9 and 10 | 0.75% | G1814A | E404= | | | 3 | 4 |
| WAXY 7A | 9 and 10 | 0.75% | G1823A | K407= | | | 3 | 4 |
| WAXY 7A | 9 and 10 | 0.75% | G1823A | K407= | | | 3 | 4 |

TABLE 3-continued

| Gene | Primer SEQ IDs. | EMS Treatment | Nucleotide Mutation According to SEQ ID | Amino Acid Mutation | PSSM Score | SIFT Score | Nucleotide Numbered According to SEQ ID NO: | Amino Acid Numbered According to SEQ ID NO: |
|---|---|---|---|---|---|---|---|---|
| WAXY 7A | 9 and 10 | 0.75% | C1851T | P417S | 12.8 | 0.12 | 3 | 4 |
| WAXY 7A | 9 and 10 | 0.75% | G1868A | E422= | | | 3 | 4 |
| WAXY 7A | 9 and 10 | 0.75% | G1868A | E422= | | | 3 | 4 |
| WAXY 7A | 9 and 10 | 0.75% | C1890T | L430= | | | 3 | 4 |
| WAXY 7A | 9 and 10 | 0.75% | C1907T | Intron | | | 3 | 4 |
| WAXY 7A | 9 and 10 | 0.75% | G1951A | Intron | | | 3 | 4 |
| WAXY 7A | 9 and 10 | 1.00% | G1960A | Intron | | | 3 | 4 |
| WAXY 7A | 11 and 12 | 0.75% | C1990T | G431= | | | 3 | 4 |
| WAXY 7A | 11 and 12 | 0.75% | G1995A | G433E | | 0.00 | 3 | 4 |
| WAXY 7A | 11 and 12 | 1.00% | C2042T | P449S | 18.4 | 0.05 | 3 | 4 |
| WAXY 7A | 11 and 12 | 0.75% | G2060A | V455M | 20.1 | 0.05 | 3 | 4 |
| WAXY 7A | 11 and 12 | 0.75% | C2100T | A468V | 16.4 | 0.00 | 3 | 4 |
| WAXY 7A | 11 and 12 | 0.75% | G2103A | G469D | 28.6 | 0.00 | 3 | 4 |
| WAXY 7A | 11 and 12 | 0.75% | C2122T | V475= | | | 3 | 4 |
| WAXY 7A | 11 and 12 | 0.75% | C2134T | F479= | | | 3 | 4 |
| WAXY 7A | 11 and 12 | 1.00% | C2152T | I485= | | | 3 | 4 |
| WAXY 7A | 11 and 12 | 0.75% | C2152T | I485= | | | 3 | 4 |
| WAXY 7A | 11 and 12 | 0.75% | G2155A | Q486= | | | 3 | 4 |
| WAXY 7A | 11 and 12 | 0.75% | G2180A | Splice | | | 3 | 4 |
| WAXY 7A | 11 and 12 | 1.00% | G2180A | Splice | | | 3 | 4 |
| WAXY 7A | 11 and 12 | 0.75% | G2199A | Intron | | | 3 | 4 |
| WAXY 7A | 11 and 12 | 0.75% | C2224T | Intron | | | 3 | 4 |
| WAXY 7A | 11 and 12 | 0.75% | C2255T | Intron | | | 3 | 4 |
| WAXY 7A | 11 and 12 | 0.75% | G2274A | C496Y | 32.7 | 0.03 | 3 | 4 |
| WAXY 7A | 11 and 12 | 0.75% | C2283T | A499V | 22.0 | 0.09 | 3 | 4 |
| WAXY 7A | 11 and 12 | 0.75% | G2284A | A499= | | | 3 | 4 |
| WAXY 7A | 11 and 12 | 0.75% | G2292A | G502D | 19.2 | 0.00 | 3 | 4 |
| WAXY 7A | 11 and 12 | 1.00% | G2315A | E510K | | 0.01 | 3 | 4 |
| WAXY 7A | 11 and 12 | 0.75% | G2329A | G514= | | | 3 | 4 |
| WAXY 7A | 11 and 12 | 0.75% | C2393T | Intron | | | 3 | 4 |
| WAXY 7A | 11 and 12 | 0.75% | G2449A | Intron | | | 3 | 4 |
| WAXY 7D | 13 and 14 | 1.00% | C783T | Intron | | | 5 | 6 |
| WAXY 7D | 13 and 14 | 0.75% | G785A | Intron | | | 5 | 6 |
| WAXY 7D | 13 and 14 | 1.00% | G785A | Intron | | | 5 | 6 |
| WAXY 7D | 13 and 14 | 0.75% | G835A | G178= | | | 5 | 6 |
| WAXY 7D | 13 and 14 | 0.75% | G851A | D184N | | 0.15 | 5 | 6 |

TABLE 3-continued

| Gene | Primer SEQ IDs. | EMS Treatment | Nucleotide Mutation According to SEQ ID | Amino Acid Mutation | PSSM Score | SIFT Score | Nucleotide Numbered According to SEQ ID NO: | Amino Acid Numbered According to SEQ ID NO: |
|---|---|---|---|---|---|---|---|---|
| WAXY 7D | 13 and 14 | 1.00% | G851A | D184N | | 0.15 | 5 | 6 |
| WAXY 7D | 13 and 14 | 1.00% | G860T | D187Y | 31.4 | 0.00 | 5 | 6 |
| WAXY 7D | 13 and 14 | 0.75% | G879A | S193N | 18.6 | 0.04 | 5 | 6 |
| WAXY 7D | 13 and 14 | 1.00% | C884T | L195F | 0.3 | 0.41 | 5 | 6 |
| WAXY 7D | 13 and 14 | 0.75% | C890T | Q197* | | | 5 | 6 |
| WAXY 7D | 13 and 14 | 1.00% | G896A | A199T | | 0.00 | 5 | 6 |
| WAXY 7D | 13 and 14 | 1.00% | G957A | Splice | | | 5 | 6 |
| WAXY 7D | 13 and 14 | 1.00% | C964T | Intron | | | 5 | 6 |
| WAXY 7D | 13 and 14 | 1.00% | C964T | Intron | | | 5 | 6 |
| WAXY 7D | 13 and 14 | 1.00% | C992T | Intron | | | 5 | 6 |
| WAXY 7D | 13 and 14 | 1.00% | G1026A | Intron | | | 5 | 6 |
| WAXY 7D | 13 and 14 | 1.00% | G1026A | Intron | | | 5 | 6 |
| WAXY 7D | 13 and 14 | 0.75% | C1055T | Intron | | | 5 | 6 |
| WAXY 7D | 13 and 14 | 0.75% | C1099T | Intron | | | 5 | 6 |
| WAXY 7D | 13 and 14 | 0.75% | G1108A | Splice | | | 5 | 6 |
| WAXY 7D | 13 and 14 | 1.00% | G1109A | G219E | | 0.00 | 5 | 6 |
| WAXY 7D | 13 and 14 | 0.75% | G1130A | C226Y | 18.0 | 0.00 | 5 | 6 |
| WAXY 7D | 13 and 14 | 0.75% | G1147A | G232S | 9.2 | 0.00 | 5 | 6 |
| WAXY 7D | 13 and 14 | 1.00% | G1148A | G232D | 12.0 | 0.00 | 5 | 6 |
| WAXY 7D | 13 and 14 | 0.75% | G1160A | C236Y | 30.6 | 0.00 | 5 | 6 |
| WAXY 7D | 13 and 14 | 0.75% | C1161T | C236= | | | 5 | 6 |
| WAXY 7D | 13 and 14 | 0.75% | G1170A | K239= | | | 5 | 6 |
| WAXY 7D | 13 and 14 | 0.75% | C1184T | S244F | 17.8 | 0.00 | 5 | 6 |
| WAXY 7D | 13 and 14 | 0.75% | C1185T | S244= | | | 5 | 6 |
| WAXY 7D | 13 and 14 | 0.75% | G1200A | R249= | | | 5 | 6 |
| WAXY 7D | 13 and 14 | 0.75% | C1222T | Intron | | | 5 | 6 |
| WAXY 7D | 13 and 14 | 0.75% | C1244T | Intron | | | 5 | 6 |
| WAXY 7D | 13 and 14 | 1.00% | C1244T | Intron | | | 5 | 6 |
| WAXY 7D | 13 and 14 | 1.00% | C1266T | Intron | | | 5 | 6 |
| WAXY 7D | 13 and 14 | 1.00% | G1269A | Intron | | | 5 | 6 |
| WAXY 7D | 13 and 14 | 0.75% | C1279T | Intron | | | 5 | 6 |
| WAXY 7D | 15 and 16 | 0.75% | G1313A | Intron | | | 5 | 6 |
| WAXY 7D | 15 and 16 | 0.75% | C1348T | Intron | | | 5 | 6 |
| WAXY 7D | 15 and 16 | 1.00% | G1351A | V253M | 19.3 | 0.01 | 5 | 6 |
| WAXY 7D | 15 and 16 | 0.75% | C1404T | D270= | | | 5 | 6 |
| WAXY 7D | 15 and 16 | 0.75% | C1419T | N275= | | | 5 | 6 |

TABLE 3-continued

| Gene | Primer SEQ IDs. | EMS Treatment | Nucleotide Mutation According to SEQ ID | Amino Acid Mutation | PSSM Score | SIFT Score | Nucleotide Numbered According to SEQ ID NO: | Amino Acid Numbered According to SEQ ID NO: |
|---|---|---|---|---|---|---|---|---|
| WAXY 7D | 15 and 16 | 0.75% | C1424T | P277L |  | 0.00 | 5 | 6 |
| WAXY 7D | 15 and 16 | 0.75% | G1430A | R279K |  | 0.23 | 5 | 6 |
| WAXY 7D | 15 and 16 | 1.00% | G1430A | R279K |  | 0.23 | 5 | 6 |
| WAXY 7D | 15 and 16 | 0.75% | G1477A | E295K | −6.8 | 1.00 | 5 | 6 |
| WAXY 7D | 15 and 16 | 0.75% | G1488A | K298= |  |  | 5 | 6 |
| WAXY 7D | 15 and 16 | 0.75% | C1491T | I299= |  |  | 5 | 6 |
| WAXY 7D | 15 and 16 | 0.75% | C1494T | N300= |  |  | 5 | 6 |
| WAXY 7D | 15 and 16 | 0.75% | G1507A | G305R | 29.6 | 0.00 | 5 | 6 |
| WAXY 7D | 15 and 16 | 0.75% | G1509A | G305= |  |  | 5 | 6 |
| WAXY 7D | 15 and 16 | 0.75% | G1518A | Q308= |  |  | 5 | 6 |
| WAXY 7D | 15 and 16 | 0.75% | G1528A | V312M |  | 0.00 | 5 | 6 |
| WAXY 7D | 15 and 16 | 0.75% | C1535T | T314M | 25.8 | 0.00 | 5 | 6 |
| WAXY 7D | 15 and 16 | 0.75% | C1545T | P317= |  |  | 5 | 6 |
| WAXY 7D | 15 and 16 | 0.75% | G1557A | E321= |  |  | 5 | 6 |
| WAXY 7D | 15 and 16 | 0.75% | G1558A | E322K | 29.0 | 0.00 | 5 | 6 |
| WAXY 7D | 15 and 16 | 0.75% | G1558A | E322K | 29.0 | 0.00 | 5 | 6 |
| WAXY 7D | 15 and 16 | 1.00% | C1566T | I324= |  |  | 5 | 6 |
| WAXY 7D | 15 and 16 | 1.00% | C1566T | I324= |  |  | 5 | 6 |
| WAXY 7D | 15 and 16 | 0.75% | G1571A | G326D | 7.8 | 0.11 | 5 | 6 |
| WAXY 7D | 15 and 16 | 0.75% | C1608T | R338= |  |  | 5 | 6 |
| WAXY 7D | 15 and 16 | 0.75% | C1608T | R338= |  |  | 5 | 6 |
| WAXY 7D | 15 and 16 | 0.75% | C1608T | R338= |  |  | 5 | 6 |
| WAXY 7D | 15 and 16 | 0.75% | C1622T | T343I | 13.7 | 0.05 | 5 | 6 |
| WAXY 7D | 15 and 16 | 1.00% | C1623T | T343= |  |  | 5 | 6 |
| WAXY 7D | 15 and 16 | 0.75% | G1625A | G344D | 16.0 | 0.00 | 5 | 6 |
| WAXY 7D | 15 and 16 | 0.75% | C1629T | I345= |  |  | 5 | 6 |
| WAXY 7D | 15 and 16 | 0.75% | G1630A | V346I | 10.4 | 0.04 | 5 | 6 |
| WAXY 7D | 15 and 16 | 0.75% | C1659T | D355= |  |  | 5 | 6 |
| WAXY 7D | 15 and 16 | 0.75% | C1661 | P356L | 20.9 | 0.00 | 5 | 6 |
| WAXY 7D | 15 and 16 | 0.75% | C1682T | A363V | 12.5 | 0.21 | 5 | 6 |
| WAXY 7D | 15 and 16 | 0.75% | C1682T | A363V | 12.5 | 0.21 | 5 | 6 |
| WAXY 7D | 15 and 16 | 0.75% | C1713T | Intron |  |  | 5 | 6 |
| WAXY 7D | 15 and 16 | 0.75% | C1736T | Intron |  |  | 5 | 6 |
| WAXY 7D | 15 and 16 | 1.00% | C1736T | Intron |  |  | 5 | 6 |
| WAXY 7D | 15 and 16 | 0.75% | T1737G | Intron |  |  | 5 | 6 |
| WAXY 7D | 15 and 16 | 0.75% | C1749T | Intron |  |  | 5 | 6 |

TABLE 3-continued

| Gene | Primer SEQ IDs. | EMS Treatment | Nucleotide Mutation According to SEQ ID | Amino Acid Mutation | PSSM Score | SIFT Score | Nucleotide Numbered According to SEQ ID NO: | Amino Acid Numbered According to SEQ ID NO: |
|---|---|---|---|---|---|---|---|---|
| WAXY 7D | 15 and 16 | 0.75% | G1758A | Intron | | | 5 | 6 |
| WAXY 7D | 15 and 16 | 0.75% | C1774T | Intron | | | 5 | 6 |
| WAXY 7D | 15 and 16 | 1.00% | C1774T | Intron | | | 5 | 6 |
| WAXY 7D | 15 and 16 | 0.75% | G1840A | G387= | | | 5 | 6 |
| WAXY 7D | 15 and 16 | 0.75% | G1843A | L388= | | | 5 | 6 |
| WAXY 7D | 15 and 16 | 1.00% | C1844T | P389S | 16.3 | 0.01 | 5 | 6 |
| WAXY 7D | 15 and 16 | 0.75% | C1865T | L396= | | | 5 | 6 |
| WAXY 7D | 15 and 16 | 0.75% | G1897A | Q406= | | | 5 | 6 |
| WAXY 7D | 15 and 16 | 0.75% | C1905T | P409L | 13.7 | 0.13 | 5 | 6 |
| WAXY 7D | 15 and 16 | 1.00% | C1905T | P409L | 13.7 | 0.13 | 5 | 6 |
| WAXY 7D | 15 and 16 | 0.75% | G1907A | D410N | 13.5 | 0.00 | 5 | 6 |
| WAXY 7D | 15 and 16 | 0.75% | C1918T | I413= | | | 5 | 6 |
| WAXY 7D | 15 and 16 | 0.75% | G1970A | Splice | | | 5 | 6 |

TABLE 4

| Gene | Primer SEQ ID NOs. | EMS Treatment | Nucleotide Mutation According to SEQ ID | Amino Acid Mutation | PSSM Score | SIFT Score | Nucleotide Numbered According to SEQ ID NO: | Amino Acid Numbered According to SEQ ID NO: |
|---|---|---|---|---|---|---|---|---|
| WAXY 7A | 7 and 8 | 0.075% | G789A | V168I | | 0.00 | 3 | 4 |
| WAXY 7A | 7 and 8 | 0.075% | G794A | R169= | | | 3 | 4 |
| WAXY 7A | 7 and 8 | 0.075% | C802T | T172I | | 0.06 | 3 | 4 |
| WAXY 7A | 7 and 8 | 0.075% | G812A | K175= | | | 3 | 4 |
| WAXY 7A | 7 and 8 | 0.075% | C860T | R191= | | | 3 | 4 |
| WAXY 7A | 7 and 8 | 0.075% | C860T | R191= | | | 3 | 4 |
| WAXY 7A | 7 and 8 | 0.075% | G899A | R204= | | | 3 | 4 |
| WAXY 7A | 7 and 8 | 0.075% | G899A | R204= | | | 3 | 4 |
| WAXY 7A | 7 and 8 | 0.075% | C1050T | Intron | | | 3 | 4 |
| WAXY 7A | 7 and 8 | 0.075% | G1057A | Intron | | | 3 | 4 |
| WAXY 7A | 7 and 8 | 0.075% | G1069A | G219= | | | 3 | 4 |
| WAXY 7A | 7 and 8 | 0.075% | C1181T | Intron | | | 3 | 4 |
| WAXY 7A | 7 and 8 | 0.075% | C1196T | Intron | | | 3 | 4 |
| WAXY 7A | 7 and 8 | 0.075% | G1228A | Intron | | | 3 | 4 |
| WAXY 7A | 9 and 10 | 0.075% | G1394A | E295K | −7.9 | 1.00 | 3 | 4 |
| WAXY 7A | 9 and 10 | 0.075% | C1402T | R297= | | | 3 | 4 |
| WAXY 7A | 9 and 10 | 0.075% | G1435A | Q308= | | | 3 | 4 |

TABLE 4-continued

| Gene | Primer SEQ ID NOs. | EMS Treatment | Nucleotide Mutation According to SEQ ID | Amino Acid Mutation | PSSM Score | SIFT Score | Nucleotide Numbered According to SEQ ID NO: | Amino Acid Numbered According to SEQ ID NO: |
|---|---|---|---|---|---|---|---|---|
| WAXY 7A | 9 and 10 | 0.075% | G1469A | A320T | 21.5 | 0.01 | 3 | 4 |
| WAXY 7A | 9 and 10 | 0.075% | C1485T | S325F | 25.4 | 0.00 | 3 | 4 |
| WAXY 7A | 9 and 10 | 0.075% | G1490A | E327K | 18.7 | 0.11 | 3 | 4 |
| WAXY 7A | 9 and 10 | 0.075% | G1522A | M337I | 1.1 | 1.00 | 3 | 4 |
| WAXY 7A | 9 and 10 | 0.075% | G1572A | W354* | | | 3 | 4 |
| WAXY 7A | 9 and 10 | 0.075% | C1633T | Intron | | | 3 | 4 |
| WAXY 7A | 9 and 10 | 0.075% | C1638T | Intron | | | 3 | 4 |
| WAXY 7A | 9 and 10 | 0.075% | G1647A | Intron | | | 3 | 4 |
| WAXY 7A | 9 and 10 | 0.075% | G1721A | E373= | | | 3 | 4 |
| WAXY 7A | 9 and 10 | 0.075% | G1897A | Intron | | | 3 | 4 |
| WAXY 7A | 9 and 10 | 0.075% | C1918T | Intron | | | 3 | 4 |
| WAXY 7A | 11 and 12 | 0.075% | G2017A | L440= | | | 3 | 4 |
| WAXY 7A | 11 and 12 | 0.075% | C2042T | P449S | 18.4 | 0.05 | 3 | 4 |
| WAXY 7A | 11 and 12 | 0.075% | C2129T | R478C | 34.2 | 0.00 | 3 | 4 |
| WAXY 7A | 11 and 12 | 0.075% | G2162A | G489R | 25.3 | 0.00 | 3 | 4 |
| WAXY 7A | 11 and 12 | 0.075% | G2406A | Intron | | | 3 | 4 |
| WAXY 4A | 19 and 20 | 0.075% | G1115A | V224M | 12.2 | 0.00 | 1 | 2 |
| WAXY 4A | 19 and 20 | 0.075% | C1140T | T232M | 17.8 | 0.00 | 1 | 2 |
| WAXY 4A | 19 and 20 | 0.075% | C1171T | N242= | | | 1 | 2 |
| WAXY 4A | 19 and 20 | 0.075% | C1236T | Intron | | | 1 | 2 |
| WAXY 4A | 19 and 20 | 0.075% | C1265T | Intron | | | 1 | 2 |
| WAXY 4A | 19 and 20 | 0.075% | G1405A | G297= | | | 1 | 2 |
| WAXY 4A | 19 and 20 | 0.075% | G1504A | R330= | | | 1 | 2 |
| WAXY 4A | 19 and 20 | 0.075% | G1607A | A365T | −0.1 | 0.17 | 1 | 2 |
| WAXY 4A | 17 and 18 | 0.075% | C1983T | Intron | | | 1 | 2 |
| WAXY 4A | 17 and 18 | 0.075% | G1993A | G434E | 33.7 | 0.00 | 1 | 2 |
| WAXY 4A | 17 and 18 | 0.075% | C2040T | P450S | 18.7 | 0.06 | 1 | 2 |
| WAXY 4A | 17 and 18 | 0.075% | C2040T | P450S | 18.7 | 0.06 | 1 | 2 |
| WAXY 4A | 17 and 18 | 0.075% | G2053A | R454K | 11.8 | 0.09 | 1 | 2 |
| WAXY 4A | 17 and 18 | 0.075% | C2057T | A455= | | | 1 | 2 |
| WAXY 4A | 17 and 18 | 0.075% | C2120T | V476= | | | 1 | 2 |
| WAXY 4A | 17 and 18 | 0.075% | C2154T | L488F | 24.1 | 0.00 | 1 | 2 |
| WAXY 4A | 17 and 18 | 0.075% | G2161A | G490E | 25.6 | 0.00 | 1 | 2 |

Phenotypic Analysis

Phenotype was examined in M3 progeny of an Express line carrying mutations that were predicted by bioinformatics analysis to affect gene function. The mutations were a truncation mutation in Wx-7D (Q197*) which was predicted to result in premature termination of the protein and a missense mutation in the Wx-7A homoeolog (A468V) which was predicted to severely affect protein function by a SIFT score of 0.00 and a change in PSSM score of 16.4. Since the Express line lacks the Wx-4A homoeolog, progeny that were homozygous for both mutations were predicted to display nearly a full waxy phenotype. Iodine was used to stain the endosperm of the progeny. Waxy endosperm stains a reddish brown with iodine, whereas amylose-containing endosperm stains very dark blue (Nakamura et al., *Mol. Gen. Genet.* 248: 253-259, 1995). Seeds were soaked in water for three hours, cut in half, and then treated with a four-fold dilution of iodine stain for 15 minutes. In contrast to seeds of the parental Express line that stained very dark blue, seeds of the double homozygous mutant stained very light blue with iodine indicating that amylose levels were significantly reduced by the mutations. These findings are consistent with the effect on protein function predicted by the mutations' SIFT and POSSUM scores.

Deposit Information

If deemed necessary by the Commissioner of Patents and Trademarks or any persons acting on his behalf, Applicants will make a deposit of at least 2500 seeds for each of the wheat varieties containing an exemplary mutation described in this application with the American Type Culture Collection (ATCC). The seeds deposited with the ATCC will be taken from the deposit maintained by Anawah Inc., 1102 Columbia Street, Suite 600, Seattle, Wash., 98104, since prior to the filing date of this application. Access to this deposit will be available during the pendency of the application to the Commissioner of Patents and Trademarks and persons determined by the Commissioner to be entitled thereto upon request. Upon allowance of any claims in the application and if designated by the Commissioner of Patents and Trademarks as a condition for allowance of those claims, Applicants will make the deposit available to the public pursuant to 37 CFR 1.808. All deposits related to this application will be maintained in the ATCC depository, which is a public depository, for a period of 30 years, or 5 years after the most recent request, or for the enforceable life of the patent, whichever is longer, and will be replaced if it becomes nonviable during that period. Additionally, Applicants have or will satisfy all requirements of 37 CFR Sections 1.801-1.809, including providing an indication of the viability of the sample upon deposit. Applicants have no authority to waive any restrictions imposed by law o the transfer of biological material or its transportation in commerce. Applicants do not waive any infringement of their rights granted under this patent or under the Plant Variety Protection Act (7 USC 2321 et seq.).

The above examples are provided to illustrate the invention but not limit its scope. Other variants of the invention will be readily apparent to one of ordinary skill in the art and are encompassed by the appended claims and all their equivalents. All publications, patents, and patent applications cited herein are hereby incorporated by reference.

We claim:

1. A method of producing a tetraploid or hexaploid wheat plant, or part thereof, exhibiting reduced waxy enzyme activity compared to a wild type wheat plant or part thereof, said method comprising the steps of:
   a) obtaining plant material from a parent wheat plant, wherein the parent wheat plant comprises two or more wild-type waxy genes;
   b) creating mutagenized plant material by inducing at least one mutation in each of the at least two waxy genes of the parent plant material, wherein said mutations are induced by treating the wheat plant material with a mutagen;
   c) analyzing the mutagenized wheat plant material, or a progeny wheat plant produced from the mutagenized wheat plant material, to identify a plant having at least one mutation in each of the at least two waxy genes, wherein said analysis is performed by isolating genomic DNA from the mutagenized wheat plant material, or a progeny wheat plant produced from the mutagenized wheat plant material, and amplifying segments of a waxy gene in the isolated genomic DNA by using primers specific to the waxy gene or to the DNA sequences adjacent to the waxy gene, wherein one of the at least two mutated waxy genes being identified encodes a protein comprising a A468V mutation in SEQ ID NO: 4, and one of the at least two mutated waxy genes being identified encodes a protein comprising a Q197* truncation mutation in SEQ ID NO: 6; and
   d) producing a tetraploid or hexaploid progeny wheat plant from the mutagenized wheat plant material or the progeny wheat plant produced from the mutagenized wheat plant material, each comprising the at least two mutated waxy genes as identified in step c), wherein the A468V mutation in SEQ ID NO: 4 and the Q197* truncation mutation in SEQ ID NO: 6 cause a reduction waxy enzyme activity in the progeny wheat plant compared to the parent wheat plant of step a), as indicated by a reduced level of amylose in the progeny wheat plant or a part thereof.

2. The method of claim 1 wherein the wheat plant material is selected from the group consisting of seeds, pollen, plant cells, and plant tissue.

3. The method of claim 1 wherein the mutagen is ethyl methanesulfonate.

4. The method of claim 3 wherein the concentration of ethyl methanesulfonate used is from about 0.75% to about 1.2%.

5. The method of claim 1 wherein analyzing the mutagenized plant material or a progeny wheat plant produced from the mutagenized wheat plant material further comprises analysis of a starch characteristic.

6. The method of claim 5 wherein the analysis of a starch characteristic comprises iodine staining.

7. The method of claim 1 wherein the part thereof is a seed.

* * * * *

```
SEQUENCE LISTING

<160> NUMBER OF SEQ ID NOS: 20

<210> SEQ ID NO 1
<211> LENGTH: 2818
<212> TYPE: DNA
<213> ORGANISM: Triticum aestivum

<400> SEQUENCE: 1
cctgcgcgcg cgatggcggc tctggtcacg tcgcagctcg ccacctccgg caccgtcctc     60
ggcatcaccg acaggttccg gcgtgcaggt tttcagggtg tgaggcccg gagcccggca    120 gatgcgccgc tcggcatgag gactaccgga gcgagcgccg ccccgaagca acaaagccgg    180
aaagcgcacc gcgggacccg gcggtgcctc tccatggtgg tgcgcgccac gggcagcgcc    240
ggcatgaacc tcgtgttcgt cggcgccgag atggcgccct ggagcaagac cggcggcctc    300
ggcgacgtcc tcggggggcct ccccccagcc atggccgtaa gctagctagc tagcaccact    360
gtcttctgat aatgtttctt cttgcagcca gccatgcctg ccattacaag tttacaactg    420
atgctgtgtc tgcaggccaa cggtcaccgg gtcatggtca tctccccgcg ctacgaccag    480
tacaaggacg cctgggacac cagcgtcgtc tccgaggtac acatatatcc gccacatgaa    540
ttatcacagt tcacatgctc ctgcacattt ctgcaaggtt ccactcaccg actggatttc    600
acagatcaag gtcgcggacg agtacgagag ggtgaggtac ttccactgct acaagcgcgg    660
ggtggaccgc gtgttcgtcg accacccgtg cttcctggag aaggtgacca atcgtcgtcg    720
tcgatcgatc aatcgatcaa gctatctttt cgtcgtctca acattcatgg tgattgattt    780
gggtgagtct ttgtttctgc tggttgcaat ttccaggtcc ggggcaagac caaggagaag    840
```

| | | | | |
|---|---|---|---|---|
| atctacgggc | ccgatgccgg | cacggactac | gaggacaacc | agctacgctt cagcctgctc | 900 |
| tgccaggcag | cgcttgaggc | acccaggatc | ctcgacctca | caacaaccc atacttctcc | 960 |
| ggaccctacg | gtaagatcaa | caacacccag | cagctactag | agtgtctgaa gaacttgatt | 1020 |
| tcttcttgag | agcactggat | gattatcatc | ttccctgtgt | cttggtgctg ccacgccatg | 1080 |
| ctatgccgcg | ccacgccgcg | caggggaaga | cgtggtgttc | gtgtgcaacg actggcacac | 1140 |
| gggccttctg | gcctgctacc | tcaagagcaa | ctaccagtcc | agtggcatct ataggacggc | 1200 |
| caaggttttg | catcttctca | aactttatat | tctctctgca | gaattttaca ttgcaacttc | 1260 |
| atttcatgtc | caggtagcgt | tctgcatcca | caacatctcg | tatcagggcc gcttctcctt | 1320 |
| cgacgacttc | gcgcagctca | acctgcccga | caggttcaag | tcgtccttcg acttcatcga | 1380 |
| cggctacgac | aagccggtgg | aggggcgcaa | gatcaactat | atgaaggccg gatcctgca | 1440 |
| ggccgacaag | gtgctcacgg | tgagccccta | ctacgcggag | gagctcatct ccggcgaagc | 1500 |
| cagggctgc | gagctcgaca | acatcatgcg | cctcacgggc | atcaccggca tcgtcaacgg | 1560 |
| catggacgtc | agcgagtggg | accccgccaa | ggacaagttc | ctcgccgcca actacgacgt | 1620 |
| caccaccgtg | agcacccgcc | cacccacaca | cccacacaaa | gatttcttcc ggtgattgct | 1680 |
| ggttctgggt | gggttctgac | ggacgaggca | aagtgacagg | cgttggaggg gaaggcgctg | 1740 |
| aacaaggagg | cgctgcaggc | cgaggtgggg | ctgccggtgg | accggaaggt gcccctggtg | 1800 |
| gccttcatcg | gcaggctgga | ggagcagaag | ggccccgacg | tgatgatcgc cgccatcccg | 1860 |
| gagatcttga | aggaggagga | cgtccagatc | gttctcctgg | tacgtcatcg accccaaccg | 1920 |
| caacccgacc | gccattgctg | aagcttcaat | caagcagacc | taaggaatga tcggatgcat | 1980 |
| tgcagggcac | cgggaagaag | aagtttgagc | ggctgctcaa | gagcgtggag gagaagttcc | 2040 |
| cgagcaaggt | gagggccgtg | gtcaggttca | acgcgccgct | ggctcaccag atgatggccg | 2100 |
| gcgccgacgt | gctcgccgtc | accagccgct | tcgagccctg | cggcctcatc cagctccagg | 2160 |
| ggatgcgcta | cggaacggta | aacgccgcct | cctccttcct | gccgattcct tatctccccg | 2220 |
| cgtatccatg | ccatgaccg | aagtttcttt | caaatttgca | gccgtgcgcg tgcgcgtcca | 2280 |
| ccggcgggct | cgtcgacacg | atcatggagg | gcaagaccgg | gttccacatg ggccgcctca | 2340 |
| gcgtcgacgt | aggctcgtcg | atcccttgtg | taaattcttc | attttgttca tcctgggagc | 2400 |
| tcaggcagat | catgaaatgg | tttcctttt | cctcttggtg | gccagtgcaa cgtggtggag | 2460 |
| ccggccgacg | tgaagaaggt | ggtgaccacc | ctgaagcgcg | ccgtcaaggt cgtcggcacg | 2520 |
| ccagcctacc | atgagatggt | caagaactgc | atgatccagg | atctctcctg gaaggtaagt | 2580 |
| cgtctctggt | ctggtttagg | atgcattttc | cagaacaact | aagagttgag actacaatgg | 2640 |
| tgctcgtgct | cgatgcatcc | attaatgtg | gcttgcgcat | atggtgcagg ggccagccaa | 2700 |
| gaactgggag | gacgtgcttc | tggaactggg | ggtcgagggg | agcgagccag gggtcatcgg | 2760 |
| cgaggagatt | gcgccgctcg | ccatggagaa | cgtcgccgct | ccctgaagag aggaaaga | 2818 |

<210> SEQ ID NO 2
<211> LENGTH: 605
<212> TYPE: PRT
<213> ORGANISM: Triticum aestivum

<400> SEQUENCE: 2

Met Ala Ala Leu Val Thr Ser Gln Leu Ala Thr Ser Gly Thr Val Leu
1               5                   10                  15

Gly Ile Thr Asp Arg Phe Arg Arg Ala Gly Phe Gln Gly Val Arg Pro
            20                  25                  30

```
Arg Ser Pro Ala Asp Ala Pro Leu Gly Met Arg Thr Thr Gly Ala Ser
         35                  40                  45

Ala Ala Pro Lys Gln Gln Ser Arg Lys Ala His Arg Gly Thr Arg Arg
     50                  55                  60

Cys Leu Ser Met Val Val Arg Ala Thr Gly Ser Ala Gly Met Asn Leu
 65                  70                  75                  80

Val Phe Val Gly Ala Glu Met Ala Pro Trp Ser Lys Thr Gly Gly Leu
                 85                  90                  95

Gly Asp Val Leu Gly Gly Leu Pro Pro Ala Met Ala Ala Asn Gly His
                100                 105                 110

Arg Val Met Val Ile Ser Pro Arg Tyr Asp Gln Tyr Lys Asp Ala Trp
            115                 120                 125

Asp Thr Ser Val Val Ser Glu Ile Lys Val Ala Asp Glu Tyr Glu Arg
        130                 135                 140

Val Arg Tyr Phe His Cys Tyr Lys Arg Gly Val Asp Arg Val Phe Val
145                 150                 155                 160

Asp His Pro Cys Phe Leu Glu Lys Val Arg Gly Lys Thr Lys Glu Lys
                165                 170                 175

Ile Tyr Gly Pro Asp Ala Gly Thr Asp Tyr Glu Asp Asn Gln Leu Arg
                180                 185                 190

Phe Ser Leu Leu Cys Gln Ala Ala Leu Glu Ala Pro Arg Ile Leu Asp
            195                 200                 205

Leu Asn Asn Asn Pro Tyr Phe Ser Gly Pro Tyr Gly Glu Asp Val Val
        210                 215                 220

Phe Val Cys Asn Asp Trp His Thr Gly Leu Leu Ala Cys Tyr Leu Lys
225                 230                 235                 240

Ser Asn Tyr Gln Ser Ser Gly Ile Tyr Arg Thr Ala Lys Val Ala Phe
                245                 250                 255

Cys Ile His Asn Ile Ser Tyr Gln Gly Arg Phe Ser Phe Asp Asp Phe
                260                 265                 270

Ala Gln Leu Asn Leu Pro Asp Arg Phe Lys Ser Ser Phe Asp Phe Ile
            275                 280                 285

Asp Gly Tyr Asp Lys Pro Val Glu Gly Arg Lys Ile Asn Trp Met Lys
        290                 295                 300

Ala Gly Ile Leu Gln Ala Asp Lys Val Leu Thr Val Ser Pro Tyr Tyr
305                 310                 315                 320

Ala Glu Glu Leu Ile Ser Gly Glu Ala Arg Gly Cys Glu Leu Asp Asn
                325                 330                 335

Ile Met Arg Leu Thr Gly Ile Thr Gly Ile Val Asn Gly Met Asp Val
            340                 345                 350

Ser Glu Trp Asp Pro Ala Lys Asp Lys Phe Leu Ala Ala Asn Tyr Asp
        355                 360                 365

Val Thr Thr Ala Leu Glu Gly Lys Ala Leu Asn Lys Glu Ala Leu Gln
370                 375                 380

Ala Glu Val Gly Leu Pro Val Asp Arg Lys Val Pro Leu Val Ala Phe
385                 390                 395                 400

Ile Gly Arg Leu Glu Glu Gln Lys Gly Pro Asp Val Met Ile Ala Ala
                405                 410                 415

Ile Pro Glu Ile Leu Lys Glu Glu Asp Val Gln Ile Val Leu Leu Gly
            420                 425                 430

Thr Gly Lys Lys Lys Phe Glu Arg Leu Leu Lys Ser Val Glu Glu Lys
        435                 440                 445

Phe Pro Ser Lys Val Arg Ala Val Val Arg Phe Asn Ala Pro Leu Ala
450                 455                 460
```

```
His Gln Met Met Ala Gly Ala Asp Val Leu Ala Val Thr Ser Arg Phe
465                 470                 475                 480

Glu Pro Cys Gly Leu Ile Gln Leu Gln Gly Met Arg Tyr Gly Thr Pro
                485                 490                 495

Cys Ala Cys Ala Ser Thr Gly Gly Leu Val Asp Thr Ile Met Glu Gly
                500                 505                 510

Lys Thr Gly Phe His Met Gly Arg Leu Ser Val Asp Cys Asn Val Val
            515                 520                 525

Glu Pro Ala Asp Val Lys Lys Val Val Thr Thr Leu Lys Arg Ala Val
            530                 535                 540

Lys Val Val Gly Thr Pro Ala Tyr His Glu Met Val Lys Asn Cys Met
545                 550                 555                 560

Ile Gln Asp Leu Ser Trp Lys Gly Pro Ala Lys Asn Trp Glu Asp Val
                565                 570                 575

Leu Leu Glu Leu Gly Val Glu Gly Ser Glu Pro Gly Val Ile Gly Glu
                580                 585                 590

Glu Ile Ala Pro Leu Ala Met Glu Asn Val Ala Ala Pro
            595                 600                 605

<210> SEQ ID NO 3
<211> LENGTH: 2805
<212> TYPE: DNA
<213> ORGANISM: Triticum aestivum

<400> SEQUENCE: 3
cctgcgcgcg ccatggcggc tctggtcacg tcccagctcg ccacctccgg caccgtcctc      60
agcgtcaccg acagattccg gcgtccaggt tttcagggcc tgaggccccg gaacccggcg     120
gatgcggcgc tcggcatgag gactgtcgga gcagcgccgc cccaaaagca aagcaggaaa     180
ccgcaccgat tcgaccggcg gtgcctctcc atggtggtgc gcgccacggg cagcggcggc     240
atgaacctcg tgttcgtcgg cgccgagatg gcgccctgga gcaagactgg cggcctcggc     300
gacgtcctcg ggggcctccc cgccgccatg gccgtaagct tgcgccactg ccttcttata     360
aatgtttctt cctgcagcca tgcctgccgt tacaacgggt gccgtgtccg tgcaggccaa     420
cggtcaccgg gtcatggtca tctccccgcg ctacgaccag tacaaggacg cctgggacac     480
cagcgtcatc tccgaggtat atatccgcca catgaattat cacaattcac atgctcctgc     540
acatttctgc aagactttac tgactggctg gatctcgcag atcaaggtcg ttgacaggta     600
cgagagggtg aggtacttcc actgctacaa gcgcggggtg gaccgcgtgt tcgtcgacca     660
cccgtgcttc ctggagaagg tgaccgatcg ctccgccgtcg atcgatcaag ctagctcctc     720
gtcgtctcaa cccgcatggt gtttgataat tcagtgagt ctttgcgtct gctggttaca     780
atttccaggt ccggggcaag accaaggaga agatctatgg acccgacgcc ggcaccgact     840
acgaggacaa ccagcagcgc ttcagccttc tctgccagga agcacttgag gtgcccagga     900
tcctcgacct caacaacaac ccacactttt ctggacccta cggtaagatc aagaacaact     960
agagtgtatc tgaagaactt gatttctact tgagagcact ggatgattat catcttcctt    1020
gtatcttggt gctgccatgc tatgccgtgc cgtgccgcgc cgcgcagggg aagacgtggt    1080
gtttgtgtgc aacgactggc acacgggcct tctggcctgc tacctcaaga gcaactacca    1140
gtccaatggc atctatagga cggccaaggt tttgcatctt ctgaaacttt atattcgctc    1200
tgcatatcaa ttttgcggtt cattctggca gcctgaattt acattgcaa ctccatttca    1260
tggctaggtg gcattctgca tccacaacat ctcgtaccag ggccgcttct ccttcgacga    1320
```

```
cttcgcgcag ctcaacctgc ctgacaggtt caagtcgtcc ttcgacttca tcgacggcta    1380
cgacaagccg gtggagggc gcaagatcaa ctggatgaag gccgggatcc tgcaggccga    1440
caaggtgctg actgtgagcc cctactatgc tgaggagcta atctctggcg aagccagggg    1500
ctgcgagctc gacaacatca tgcgcctcac tgggatcacc ggcatcgtca acggcatgga    1560
cgtcagcgag tgggacccca tcaaggacaa gttcctcacc gtcaactacg acgtcaccac    1620
cgtgagcacc cacccaccca cacaaagatt tcttccggtg atcgctggtt ctgggtggat    1680
tctgagttct gacaaacgag gcaaagtgac aggcgttgga ggggaaggcg ctgaacaagg    1740
aggcgctgca ggccgaggtg gggctgccgg tggaccggaa ggtgcccctg gtggcgttca    1800
tcggcaggct ggaggagcag aagggccccg acgtgatgat cgccgccatc ccggagatcg    1860
tgaaggagga ggacgtccag atcgttctcc tggtacgatc gaccgacatt gctgacccgt    1920
tcaggaaaat ctcctgatag ctcgccgtgg ggatgggtgg gtgactgact gatcgaatgc    1980
attgcagggc accgggaaga agaagtttga gcggctgctc aagagcgtgg aggagaagtt    2040
cccgaccaag gtgtgggccg tggtcaggtt caacgcgccg ctggctcacc agatgatggc    2100
cggcgccgac gtgctggcgg tcaccagccg cttcgagccc tgcggcctca tccagctcca    2160
gggaatgcgc tacggaacgg taaacgcatc ctccttcagt ccttcttgcc agttcctcac    2220
ctcctttgca tatccatggc catgaccgaa gtttctttca aattttcagc cgtgcgcctg    2280
cgcgtcgaca ggcgggctcg tcgacactat cgtggaaggc aagaccgggt tccacatggg    2340
ccgcctcagc gttgacgtat gctcatcgat cctcttgtat acattcattc atcttgttca    2400
tcatggcagc tcagacagat catgaagtgg tgcacttttc ttgttggtgg ccagtgcaac    2460
gtggtggagc cggccgacgt gaagaaggtg gtcaccaccc tgaagcgcgc cgtcaaggtc    2520
gtcggcacgc cggcgtacca tgagatggtc aagaactgca tgatacagga tctctcctgg    2580
aaggtaagtc gtctctggtt cagtatgcac ttcctggaac aactaagagt gaagggccga    2640
tgtatccatt aatggtggct tgcgcatatg atgcaggggc ctgccaagaa ctgggaggac    2700
gtgcttctgg aactggggt ggaggggagc gagccgggca tcgtcggcga ggagatcgcg    2760
ccgctcgccc tggagaacgt cgccgctccc tgaagagaga agaa                    2805
```

<210> SEQ ID NO 4
<211> LENGTH: 604
<212> TYPE: PRT
<213> ORGANISM: Triticum aestivum

<400> SEQUENCE: 4

```
Met Ala Ala Leu Val Thr Ser Gln Leu Ala Thr Ser Gly Thr Val Leu
1               5                   10                  15

Ser Val Thr Asp Arg Phe Arg Arg Pro Gly Phe Gln Gly Leu Arg Pro
            20                  25                  30

Arg Asn Pro Ala Asp Ala Ala Leu Gly Met Arg Thr Val Gly Ala Ser
        35                  40                  45

Ala Ala Pro Lys Gln Ser Arg Lys Pro His Arg Phe Asp Arg Arg Cys
    50                  55                  60

Leu Ser Met Val Val Arg Ala Thr Gly Ser Gly Met Asn Leu Val
65                  70                  75                  80

Phe Val Gly Ala Glu Met Ala Pro Trp Ser Lys Thr Gly Gly Leu Gly
                85                  90                  95

Asp Val Leu Gly Gly Leu Pro Ala Ala Met Ala Ala Asn Gly His Arg
            100                 105                 110

Val Met Val Ile Ser Pro Arg Tyr Asp Gln Tyr Lys Asp Ala Trp Asp
```

-continued

```
                115                 120                 125
Thr Ser Val Ile Ser Glu Ile Lys Val Asp Arg Tyr Glu Arg Val
    130                 135                 140
Arg Tyr Phe His Cys Tyr Lys Arg Gly Val Asp Arg Val Phe Val Asp
145                 150                 155                 160
His Pro Cys Phe Leu Glu Lys Val Arg Gly Lys Thr Lys Glu Lys Ile
                165                 170                 175
Tyr Gly Pro Asp Ala Gly Thr Asp Tyr Glu Asp Asn Gln Gln Arg Phe
            180                 185                 190
Ser Leu Leu Cys Gln Ala Ala Leu Glu Val Pro Arg Ile Leu Asp Leu
        195                 200                 205
Asn Asn Asn Pro His Phe Ser Gly Pro Tyr Gly Glu Asp Val Val Phe
210                 215                 220
Val Cys Asn Asp Trp His Thr Gly Leu Leu Ala Cys Tyr Leu Lys Ser
225                 230                 235                 240
Asn Tyr Gln Ser Asn Gly Ile Tyr Arg Thr Ala Lys Val Ala Phe Cys
                245                 250                 255
Ile His Asn Ile Ser Tyr Gln Gly Arg Phe Ser Phe Asp Asp Phe Ala
            260                 265                 270
Gln Leu Asn Leu Pro Asp Arg Phe Lys Ser Ser Phe Asp Phe Ile Asp
        275                 280                 285
Gly Tyr Asp Lys Pro Val Glu Gly Arg Lys Ile Asn Trp Met Lys Ala
290                 295                 300
Gly Ile Leu Gln Ala Asp Lys Val Leu Thr Val Ser Pro Tyr Tyr Ala
305                 310                 315                 320
Glu Glu Leu Ile Ser Gly Glu Ala Arg Gly Cys Glu Leu Asp Asn Ile
                325                 330                 335
Met Arg Leu Thr Gly Ile Thr Gly Ile Val Asn Gly Met Asp Val Ser
            340                 345                 350
Glu Trp Asp Pro Ile Lys Asp Lys Phe Leu Thr Val Asn Tyr Asp Val
        355                 360                 365
Thr Thr Ala Leu Glu Gly Lys Ala Leu Asn Lys Glu Ala Leu Gln Ala
370                 375                 380
Glu Val Gly Leu Pro Val Asp Arg Lys Val Pro Leu Val Ala Phe Ile
385                 390                 395                 400
Gly Arg Leu Glu Glu Gln Lys Gly Pro Asp Val Met Ile Ala Ala Ile
                405                 410                 415
Pro Glu Ile Val Lys Glu Glu Asp Val Gln Ile Val Leu Leu Gly Thr
            420                 425                 430
Gly Lys Lys Lys Phe Glu Arg Leu Leu Lys Ser Val Glu Glu Lys Phe
        435                 440                 445
Pro Thr Lys Val Trp Ala Val Val Arg Phe Asn Ala Pro Leu Ala His
450                 455                 460
Gln Met Met Ala Gly Ala Asp Val Leu Ala Val Thr Ser Arg Phe Glu
465                 470                 475                 480
Pro Cys Gly Leu Ile Gln Leu Gln Gly Met Arg Tyr Gly Thr Pro Cys
                485                 490                 495
Ala Cys Ala Ser Thr Gly Gly Leu Val Asp Thr Ile Val Glu Gly Lys
            500                 505                 510
Thr Gly Phe His Met Gly Arg Leu Ser Val Asp Cys Asn Val Val Glu
        515                 520                 525
Pro Ala Asp Val Lys Lys Val Val Thr Thr Leu Lys Arg Ala Val Lys
530                 535                 540
```

```
Val Val Gly Thr Pro Ala Tyr His Glu Met Val Lys Asn Cys Met Ile
545                 550                 555                 560

Gln Asp Leu Ser Trp Lys Gly Pro Ala Lys Asn Trp Glu Asp Val Leu
                565                 570                 575

Leu Glu Leu Gly Val Glu Gly Ser Glu Pro Gly Ile Val Gly Glu Glu
            580                 585                 590

Ile Ala Pro Leu Ala Leu Glu Asn Val Ala Ala Pro
            595                 600

<210> SEQ ID NO 5
<211> LENGTH: 2886
<212> TYPE: DNA
<213> ORGANISM: Triticum aestivum

<400> SEQUENCE: 5
cctgcgcgcg ccatggcggc tctggtcacg tcccagctcg ccacctccgg caccgtcctc      60
ggcatcaccg acaggttccg gcgtgcaggt ttccagggcg tgaggccccg gagcccggcg     120
gatgcggctc tcggcatgag gaccgtcgga gctagcgccg ccccaacgca aagccggaaa     180
gcgcaccgcg gacccggcg tgcctctcc atggtggtgc gcgccaccgg cagcggcggc       240
atgaacctcg tgttcgtcgg cgccgagatg gcgccctgga gcaagaccgg cggcctcggc     300
gacgtcctcg ggggcctccc cccagccatg ccgtaagct agacagcacc actgtcttct     360
cataatgttc atcttgcagt tgcagccatg cctgccgtta acgggtgg tgtgtccgtg       420 caggccaacg ccaccgggt catggtcatc tccccgcgct acgaccagta caaggacgcc     480
tgggacacca gcgtcgtctc cgaggtactt gaaccctacc cgcaactttta acgatcaaaa    540 ttcgcatgct cctgcacatt tctgcaggat cctactgact gactaactgg atctcgcaga    600
tcaaggtcgt tgacaagtac gagagggtga ggtacttcca ctgctacaag gcgggggtgg   660
accgcgtgtt cgtcgaccac ccgtgcttcc tggagaaggt gaccgatcgt cgtcgtggac   720
cgatcaagct agctcttcgt cgtctcaacc ttgataggca tggtgattga tttcagttgt    780
ttctgctggt tgcaatttcc aggtccgggg caagaccaag gagaagatct acgggcccga    840
cgccggcacg gactacgagg acaaccagca gcgcttcagc cttctctgcc aggcggcgct    900
ggaagtgccg aggatcctga acctcgacaa taaccccctac ttttctgggc cctacggtaa   960
gatcaagatc aagcacgcct actagttcaa gctagagtgt gtgtaatctg aactctgaag  1020
aacttgatat tttcttgaga gagctggatg atcaccattt tttttttgtat ctgggtgccg  1080 tcgtcgtccc ttgttgcgcg ccgcgcaggg gaggacgtgg tgttcgtgtg caatgactgg  1140
cacacgggcc ttctggcctg ctacctcaag agcaactacc agtccaatgg catctacagg  1200
gccgcaaagg ttttgcatct tcttctcaaa ctatatatcc tctctgcatt catatgcatg   1260
catatcttgc tcttcattct gaaacaggca tatcaatttt gcggttcatt ctggcctgaa  1320
ttttacattg caacttcatt tcatggccag gtggcattct gcatccacaa catctcgtac  1380
cagggccgct tctccttcga cgacttcgcg cagctcaacc tgcccgacag gttcaagtcg  1440
tccttcgact tcatcgacgg ctacgacaag ccggtggagg gcgcaagat caactggatg   1500 aaggccggga tcctgcaggc cgacaaggtg ctgacggtga gccctacta cgcggaggag  1560 ctcatctctg gcgaagccag gggctgcgag ctcgacaaca tcatgcgcct cactgggatc  1620
accggcatcg tcaacggcat ggatgttagc gagtgggacc ccaccaagga caagttcctc  1680
gccgtcaact acgacatcac caccgtgagc aaccacacaa agatttcttc ctcttcttcc  1740
ggtgatcgct ggttctgggt gggttctcac gaacgaggca aagtgacagg cgttggaggg  1800
```

-continued

```
gaaggcgctg aacaaggagg cgctgcaggc cgaggtgggg ctgccggtgg accggaaggt    1860
gcccctggtg gcgttcatcg gcaggctgga ggagcagaag ggccccgacg tgatgatcgc    1920
cgccatcccg gagatcctga aggaggagga cgtccagatc gttctcctgg tacatcatcg    1980
agcccgcaac ccgaccgcca ttgctgaaac ttcgatcaag cagacctaag gaatgatcga    2040
atgcattgca gggcaccggg aagaagaagt tcgagcggct actcaagagc attgaggaga    2100
aattcccgag caaggtgagg gccgtggtca ggttcaacgc gccgctggct caccagatga    2160
tggccggcgc cgacgtgctc gccgtcacca gccgcttcga gccctgcggc ctcatccagc    2220 tccagggat gcgctacgga acggtaaact tttccttctt gccaagtcct tacttcctga     2280
gcaatcatga gccatgccca tgaccgaagt tcttccaaa ttttcagccg tgcgcgtgcg     2340
cgtccaccgg cgggcttgtc gacacgatcg tggaggcaa gaccgggttc cacatggggcc    2400 ggctcagtgt cgatgtaagt tcatcaatct cttcaataaa ttcttcatct tgttcatcct    2460
gggagctcag gcagatcatc aaacgggttt cctttttcct cttggtggcc agtgcaacgt    2520
ggtggagccg gccgacgtga agaaggtggt gaccacccctg aagcgcgccg tcaaggtcgt    2580
cggcacgccg gcataccatg agatggtcaa gaactgcatg atacaggatc tctcctggaa    2640
ggtaagtcag tctctggtct ggtttaggat gcattttcca gaacaactaa gagttaagac    2700
tacaatggtg ctcttgttcg atgtatccat taatggtggc ttgcgcatat ggtgcagggg    2760
ccagccaaga actgggagga cgtgcttctg gaactgggtg tcgaggggag cgagccgggg    2820
gtcatcggcg aggagattgc gccgctcgcc atggagaacg tcgccgctcc ctgaagagag    2880
aaagaa                                                               2886
```

<210> SEQ ID NO 6
<211> LENGTH: 604
<212> TYPE: PRT
<213> ORGANISM: Triticum aestivum

<400> SEQUENCE: 6

```
Met Ala Ala Leu Val Thr Ser Gln Leu Ala Thr Ser Gly Thr Val Leu
1               5                   10                  15

Gly Ile Thr Asp Arg Phe Arg Arg Ala Gly Phe Gln Gly Val Arg Pro
            20                  25                  30

Arg Ser Pro Ala Asp Ala Ala Leu Gly Met Arg Thr Val Gly Ala Ser
        35                  40                  45

Ala Ala Pro Thr Gln Ser Arg Lys Ala His Arg Gly Thr Arg Arg Cys
    50                  55                  60

Leu Ser Met Val Val Arg Ala Thr Gly Ser Gly Met Asn Leu Val
65                  70                  75                  80

Phe Val Gly Ala Glu Met Ala Pro Trp Ser Lys Thr Gly Gly Leu Gly
                85                  90                  95

Asp Val Leu Gly Gly Leu Pro Pro Ala Met Ala Ala Asn Gly His Arg
            100                 105                 110

Val Met Val Ile Ser Pro Arg Tyr Asp Gln Tyr Lys Asp Ala Trp Asp
        115                 120                 125

Thr Ser Val Val Ser Glu Ile Lys Val Val Asp Lys Tyr Glu Arg Val
    130                 135                 140

Arg Tyr Phe His Cys Tyr Lys Arg Gly Val Asp Arg Val Phe Val Asp
145                 150                 155                 160

His Pro Cys Phe Leu Glu Lys Val Arg Gly Lys Thr Lys Glu Lys Ile
                165                 170                 175

Tyr Gly Pro Asp Ala Gly Thr Asp Tyr Glu Asp Asn Gln Gln Arg Phe
```

-continued

```
                180                 185                 190
Ser Leu Leu Cys Gln Ala Ala Leu Glu Val Pro Arg Ile Leu Asn Leu
            195                 200                 205
Asp Asn Asn Pro Tyr Phe Ser Gly Pro Tyr Gly Glu Asp Val Val Phe
        210                 215                 220
Val Cys Asn Asp Trp His Thr Gly Leu Leu Ala Cys Tyr Leu Lys Ser
225                 230                 235                 240
Asn Tyr Gln Ser Asn Gly Ile Tyr Arg Ala Ala Lys Val Ala Phe Cys
            245                 250                 255
Ile His Asn Ile Ser Tyr Gln Gly Arg Phe Ser Phe Asp Asp Phe Ala
        260                 265                 270
Gln Leu Asn Leu Pro Asp Arg Phe Lys Ser Ser Phe Asp Phe Ile Asp
            275                 280                 285
Gly Tyr Asp Lys Pro Val Glu Gly Arg Lys Ile Asn Trp Met Lys Ala
        290                 295                 300
Gly Ile Leu Gln Ala Asp Lys Val Leu Thr Val Ser Pro Tyr Tyr Ala
305                 310                 315                 320
Glu Glu Leu Ile Ser Gly Glu Ala Arg Gly Cys Glu Leu Asp Asn Ile
            325                 330                 335
Met Arg Leu Thr Gly Ile Thr Gly Ile Val Asn Gly Met Asp Val Ser
        340                 345                 350
Glu Trp Asp Pro Thr Lys Asp Lys Phe Leu Ala Val Asn Tyr Asp Ile
            355                 360                 365
Thr Thr Ala Leu Glu Gly Lys Ala Leu Asn Lys Glu Ala Leu Gln Ala
        370                 375                 380
Glu Val Gly Leu Pro Val Asp Arg Lys Val Pro Leu Val Ala Phe Ile
385                 390                 395                 400
Gly Arg Leu Glu Glu Gln Lys Gly Pro Asp Val Met Ile Ala Ala Ile
            405                 410                 415
Pro Glu Ile Leu Lys Glu Asp Val Gln Ile Val Leu Leu Gly Thr
        420                 425                 430
Gly Lys Lys Lys Phe Glu Arg Leu Leu Lys Ser Ile Glu Glu Lys Phe
        435                 440                 445
Pro Ser Lys Val Arg Ala Val Val Arg Phe Asn Ala Pro Leu Ala His
        450                 455                 460
Gln Met Met Ala Gly Ala Asp Val Leu Ala Val Thr Ser Arg Phe Glu
465                 470                 475                 480
Pro Cys Gly Leu Ile Gln Leu Gln Gly Met Arg Tyr Gly Thr Pro Cys
            485                 490                 495
Ala Cys Ala Ser Thr Gly Gly Leu Val Asp Thr Ile Val Glu Gly Lys
        500                 505                 510
Thr Gly Phe His Met Gly Arg Leu Ser Val Asp Cys Asn Val Val Glu
        515                 520                 525
Pro Ala Asp Val Lys Lys Val Thr Thr Leu Lys Arg Ala Val Lys
        530                 535                 540
Val Val Gly Thr Pro Ala Tyr His Glu Met Val Lys Asn Cys Met Ile
545                 550                 555                 560
Gln Asp Leu Ser Trp Lys Gly Pro Ala Lys Asn Trp Glu Asp Val Leu
            565                 570                 575
Leu Glu Leu Gly Val Glu Gly Ser Glu Pro Gly Val Ile Gly Glu Glu
        580                 585                 590
Ile Ala Pro Leu Ala Met Glu Asn Val Ala Ala Pro
        595                 600
```

```
<210> SEQ ID NO 7
<211> LENGTH: 28
<212> TYPE: DNA
<213> ORGANISM: Artificial
<220> FEATURE:
<223> OTHER INFORMATION: Primer 7A WX 2L

<400> SEQUENCE: 7
acccgcatgg tgtttgataa tttcagtg                                              28

<210> SEQ ID NO 8
<211> LENGTH: 28
<212> TYPE: DNA
<213> ORGANISM: Artificial
<220> FEATURE:
<223> OTHER INFORMATION: Primer 7A WX 2R

<400> SEQUENCE: 8
agaatgccac ctagccatga aatggagt                                              28

<210> SEQ ID NO 9
<211> LENGTH: 26
<212> TYPE: DNA
<213> ORGANISM: Artificial
<220> FEATURE:
<223> OTHER INFORMATION: Primer 7A WX 3L

<400> SEQUENCE: 9
cgctctgcat atcaattttg cggttc                                                26

<210> SEQ ID NO 10
<211> LENGTH: 26
<212> TYPE: DNA
<213> ORGANISM: Artificial
<220> FEATURE:
<223> OTHER INFORMATION: Primer 7A WX 3R

<400> SEQUENCE: 10
cctgcaatgc attcgatcag tcagtc                                                26

<210> SEQ ID NO 11
<211> LENGTH: 27
<212> TYPE: DNA
<213> ORGANISM: Artificial
<220> FEATURE:
<223> OTHER INFORMATION: Primer 7A WX 4L

<400> SEQUENCE: 11
gttctcctgg tacgatcgac cgacatt                                               27

<210> SEQ ID NO 12
<211> LENGTH: 28
<212> TYPE: DNA
<213> ORGANISM: Artificial
<220> FEATURE:
<223> OTHER INFORMATION: Primer 7A WX 4R

<400> SEQUENCE: 12
atcggcccct cactcttagt tgttccag                                              28

<210> SEQ ID NO 13
<211> LENGTH: 31
<212> TYPE: DNA
<213> ORGANISM: Artificial
<220> FEATURE:
<223> OTHER INFORMATION: Primer 7D WX 2L
```

-continued

```
<400> SEQUENCE: 13
tcgtcgtctc aaccttgata ggcatggtga t                              31

<210> SEQ ID NO 14
<211> LENGTH: 28
<212> TYPE: DNA
<213> ORGANISM: Artificial
<220> FEATURE:
<223> OTHER INFORMATION: Primer 7D WX 2R

<400> SEQUENCE: 14
gaaccgcaaa attgatatgc ctgtttca                                  28

<210> SEQ ID NO 15
<211> LENGTH: 28
<212> TYPE: DNA
<213> ORGANISM: Artificial
<220> FEATURE:
<223> OTHER INFORMATION: Primer 7D WX 3L

<400> SEQUENCE: 15
tgaaacaggc atatcaattt tgcggttc                                  28

<210> SEQ ID NO 16
<211> LENGTH: 28
<212> TYPE: DNA
<213> ORGANISM: Artificial
<220> FEATURE:
<223> OTHER INFORMATION: Primer 7D WX 3R

<400> SEQUENCE: 16
tcgatcattc cttaggtctg cttgatcg                                  28

<210> SEQ ID NO 17
<211> LENGTH: 24
<212> TYPE: DNA
<213> ORGANISM: Artificial
<220> FEATURE:
<223> OTHER INFORMATION: Primer 4A WX 8L

<400> SEQUENCE: 17
ccacccacac acccacacaa agat                                      24

<210> SEQ ID NO 18
<211> LENGTH: 26
<212> TYPE: DNA
<213> ORGANISM: Artificial
<220> FEATURE:
<223> OTHER INFORMATION: Primer 4A WX 8R

<400> SEQUENCE: 18
tttacacaag ggatcgacga gcctac                                    26

<210> SEQ ID NO 19
<211> LENGTH: 27
<212> TYPE: DNA
<213> ORGANISM: Artificial
<220> FEATURE:
<223> OTHER INFORMATION: Primer 4A WX 6L

<400> SEQUENCE: 19
ggtaagatca acaacaccca gcagcta                                   27

<210> SEQ ID NO 20
<211> LENGTH: 28
<212> TYPE: DNA
```

```
<213> ORGANISM: Artificial
<220> FEATURE:
<223> OTHER INFORMATION: Primer 4A WX 3R

<400> SEQUENCE: 20
aaccagcaat caccggaaga aatctttg                                          28
```